United States Patent
Harshman et al.

(10) Patent No.: US 12,268,423 B2
(45) Date of Patent: Apr. 8, 2025

(54) STABILIZATION SYSTEM, IMPLANT, AND METHODS FOR PREVENTING RELATIVE MOTION BETWEEN SECTIONS OF TISSUE

(71) Applicant: Stryker Corporation, Kalamazoo, MI (US)

(72) Inventors: Gabriel Harshman, Portage, MI (US); Christopher Brockman, Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 36 days.

(21) Appl. No.: 17/941,521

(22) Filed: Sep. 9, 2022

(65) Prior Publication Data

US 2023/0000529 A1 Jan. 5, 2023

Related U.S. Application Data

(63) Continuation of application No. 16/604,828, filed as application No. PCT/US2018/028546 on Apr. 20, 2018, now Pat. No. 11,452,548.

(Continued)

(51) Int. Cl.
*A61B 17/70* (2006.01)
*A61B 17/00* (2006.01)
(Continued)

(52) U.S. Cl.
CPC .... *A61B 17/7055* (2013.01); *A61B 17/00234* (2013.01); *A61B 17/3423* (2013.01);
(Continued)

(58) Field of Classification Search
CPC ............ A61B 17/7055; A61B 17/7064; A61B 17/7065; A61B 17/7071; A61B 17/7097;
(Continued)

(56) References Cited

U.S. PATENT DOCUMENTS 7,488,320 B2 2/2009 Middleton
7,491,236 B2 * 2/2009 Cragg .................... A61F 2/441
606/301

(Continued)

FOREIGN PATENT DOCUMENTS

DE 102010041226 A1 3/2012
EP 2730246 A1 5/2014
(Continued)

OTHER PUBLICATIONS

International Search Report for Application No. PCT/US2018/028546 dated Aug. 29, 2018, 3 pages.
(Continued)

*Primary Examiner* — Eduardo C Robert
*Assistant Examiner* — Steven J Cotroneo
(74) *Attorney, Agent, or Firm* — Howard & Howard Attorneys PLLC

(57) ABSTRACT

A system for preventing relative motion between bones or sections of bone, for example, an ilium and a sacrum. The system includes an insertion tool and an implant. The implant includes a trunk, a distal anchor, a proximal anchor, and a stem coupled to the trunk. A driver of the insertion tool receives an input for a drive shaft of the insertion tool to draw the stem proximally such that the trunk is drawn towards the insertion tool. The drawing of the trunk and engagement of first and second engagement features is configured to deploy the proximal anchor outwardly. The distal anchor may be an expandable member, and the implant may define a bore extending through the proximal anchor for the distal anchor to receive injectable material. The system may be cannulated such that the insertion tool and the implant may be directed over a guidewire to position the implant.

18 Claims, 13 Drawing Sheets

Related U.S. Application Data

(60) Provisional application No. 62/488,417, filed on Apr. 21, 2017.

(51) Int. Cl.
   *A61B 17/34* (2006.01)
   *A61B 17/84* (2006.01)
   *A61B 17/56* (2006.01)

(52) U.S. Cl.
   CPC ........ *A61B 17/7098* (2013.01); *A61B 17/844* (2013.01); *A61B 2017/564* (2013.01)

(58) Field of Classification Search
   CPC .............. A61B 17/7098; A61B 17/844; A61B 2017/8655; A61B 2017/867
   See application file for complete search history.

(56) References Cited

U.S. PATENT DOCUMENTS

| | | |
|---|---|---|
| 7,789,901 B2 | 9/2010 | Froehlich |
| 8,202,305 B2 | 6/2012 | Reiley |
| 8,277,506 B2 | 10/2012 | Krueger et al. |
| 8,292,928 B2 | 10/2012 | Cragg et al. |
| 8,357,198 B2 | 1/2013 | McGraw et al. |
| 8,444,693 B2 * | 5/2013 | Reiley ................... A61F 2/4455 623/17.11 |
| 8,696,706 B2 | 4/2014 | Falahee |
| 9,017,407 B2 | 4/2015 | Donner |
| 9,039,743 B2 | 5/2015 | Reiley |
| 9,101,408 B1 | 8/2015 | Dix |
| 9,498,348 B2 | 11/2016 | Dix |
| 9,522,028 B2 | 12/2016 | Warren et al. |
| 9,788,961 B2 | 10/2017 | Donner et al. |
| 9,802,674 B2 | 10/2017 | Bachman et al. |
| 9,814,609 B2 | 11/2017 | Shaw et al. |
| 11,452,548 B2 | 9/2022 | Harshman et al. |
| 2005/0113919 A1 | 5/2005 | Cragg et al. |
| 2006/0155297 A1* | 7/2006 | Ainsworth ............ A61F 2/4425 606/99 |
| 2007/0270858 A1 | 11/2007 | Trieu et al. |
| 2008/0262502 A1 | 10/2008 | Ainsworth et al. |
| 2009/0187249 A1 | 7/2009 | Osman |
| 2010/0016905 A1* | 1/2010 | Greenhalgh ....... A61B 17/8875 606/313 |
| 2010/0036381 A1 | 2/2010 | Vanleeuwen et al. |
| 2012/0029578 A1 | 2/2012 | Suh |
| 2013/0053902 A1* | 2/2013 | Trudeau .............. A61B 17/8685 606/313 |
| 2013/0096634 A1 | 4/2013 | Suh |
| 2013/0144348 A1* | 6/2013 | Schwappach ........ A61B 17/864 606/323 |
| 2013/0218215 A1* | 8/2013 | Ginn ..................... A61B 6/032 606/86 A |
| 2013/0245703 A1 | 9/2013 | Warren et al. |
| 2013/0267836 A1* | 10/2013 | Mauldin ............ A61B 17/1671 606/96 |
| 2013/0296953 A1 | 11/2013 | Mauldin et al. |
| 2014/0046380 A1 | 2/2014 | Asfora |
| 2014/0142700 A1 | 5/2014 | Donner et al. |
| 2014/0277460 A1 | 9/2014 | Schifano et al. |
| 2015/0012051 A1 | 1/2015 | Warren et al. |
| 2015/0313720 A1* | 11/2015 | Lorio ................... A61B 17/863 623/17.11 |
| 2016/0051375 A1 | 2/2016 | Dix |
| 2016/0220275 A1* | 8/2016 | Ratron ................. A61B 17/686 |
| 2017/0035484 A1 | 2/2017 | Dix |
| 2017/0151005 A1 | 6/2017 | Warren et al. |
| 2020/0085474 A1 | 3/2020 | Harshman et al. |
| 2021/0275233 A1 | 9/2021 | Fang et al. |

FOREIGN PATENT DOCUMENTS

| | | |
|---|---|---|
| WO | 2008112308 A1 | 9/2008 |
| WO | 2010017377 A1 | 2/2010 |
| WO | 2010105196 A1 | 9/2010 |
| WO | 2012015976 A1 | 2/2012 |
| WO | 2018195406 A1 | 10/2018 |

OTHER PUBLICATIONS

Partial International Search Report for Application No. PCT/EP2011/006224 dated Jul. 5, 2018, 3 pages.

Machine-assisted English language abstract and machine-assisted English language translation for DE 10 2010 041 226 A1 extracted from espacenet.com database on Oct. 28, 2023, 10 pages.

* cited by examiner

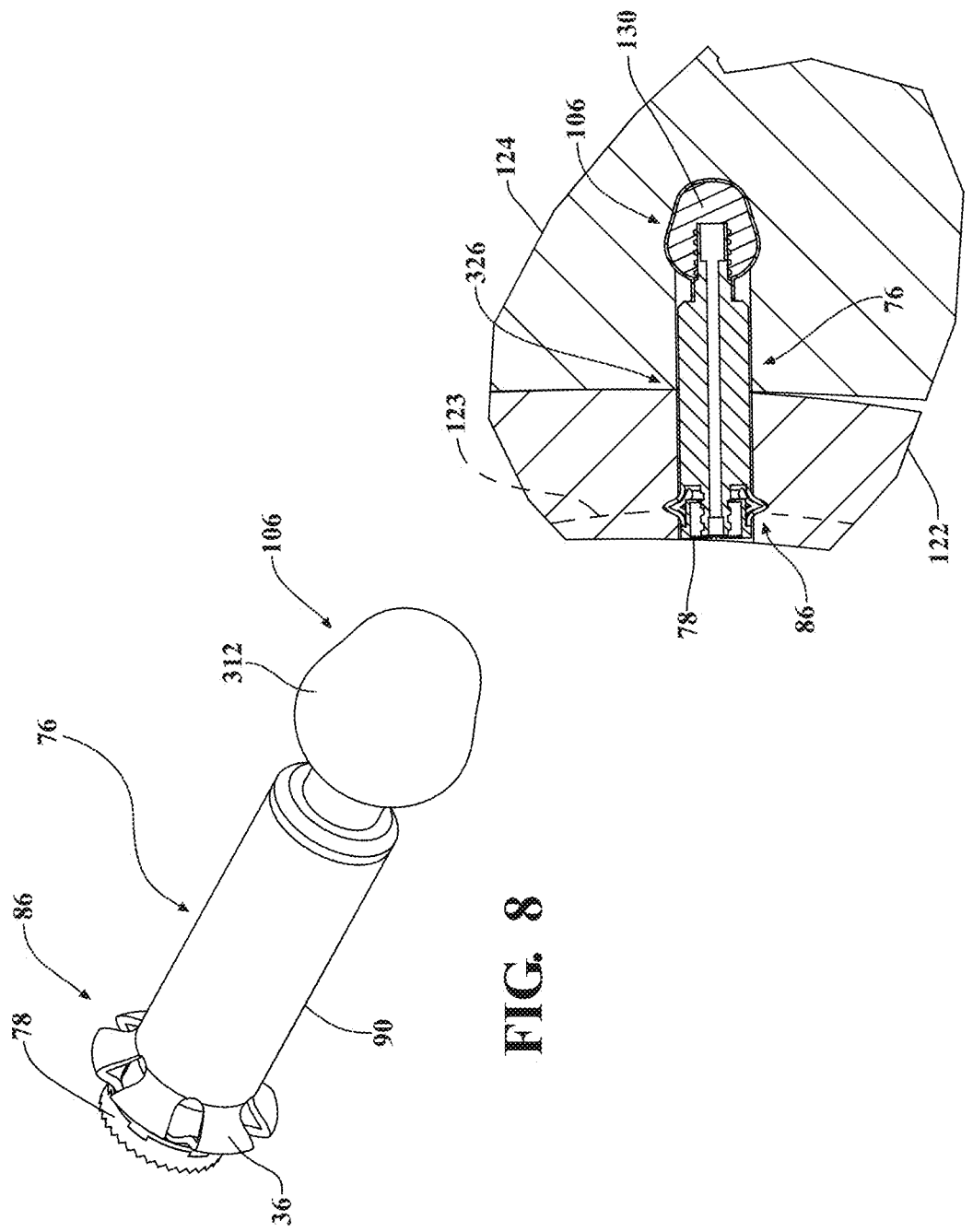

STABILIZATION SYSTEM, IMPLANT, AND METHODS FOR PREVENTING RELATIVE MOTION BETWEEN SECTIONS OF TISSUE

CROSS-REFERENCE TO RELATED APPLICATIONS

This is a continuation of copending U.S. application Ser. No. 16/604,828, filed Oct. 11, 2019, which is a national entry of International Application No. PCT/US2018/028546, filed Apr. 20, 2018, which claims priority to and all the benefits of U.S. Provisional Application No. 62/488,417, filed on Apr. 21, 2017, the entire contents of each being hereby incorporated by reference.

TECHNICAL FIELD

The present disclosure is related generally to an implant for a stabilization system for securing two sections of tissue. More particularly, but not exclusively, the present disclosure is directed to stabilization system, an implant, and methods for preventing relative motion between a first bone and a second bone, for example, an ilium and a sacrum defining a sacroiliac (SI) joint during minimally invasive surgery.

BACKGROUND

A number of different medical procedures involve securing sections of tissue. For example, for an individual to receive relief from pain in the pelvic region or lower back, a recognized treatment is to perform SI joint fusion in which the sacrum is fixed to the ilium. Another situation when it is indicated to secure two sections of tissue is fixation of a fractured bone. Still further, spinal fusion including fixation of adjacent vertebrae is also a procedure of particular interest.

Securing adjacent sections of bone (or two adjacent bones) may include drilling a bore that at least partially extends through each of the adjacent sections of the bone. An elongated implant is seated and secured within the bore. A portion of the implant is positioned in one of the sections of the bone (e.g., a first bone), and another portion of the implant is positioned within another section of the bone (e.g., a second bone). The implant, and sometimes plural implants, prevents movement of the sections of the bone. The adjacent surfaces of the sections of the bone may fuse together to form a single bone. The fusion increases the strength of the bond between the two sections of bone.

Known systems and methods of securing sections of tissue are associated with several disadvantages. For example, eliminating relative movement between the sections of the bone often requires the implant to be relatively large in size to ensure adequate contact area between the implant and the sections of the bone. It readily follows that a relatively larger implant requires a commensurately larger incision. The invasiveness of the larger incision may lead to increased healing time and risk of infection.

Therefore, there is a need in the art for a stabilization system and an implant for the stabilization system designed to overcome one or more of the aforementioned disadvantages

SUMMARY

One aspect of the present disclosure is directed toward an implant for a minimally invasive bone stabilization system for preventing relative motion between an ilium and a sacrum. The implant comprises an elongate trunk defined between a proximal end configured to be positioned within the ilium, a distal end configured to be positioned within the sacrum. The elongate trunk extends between the ilium and the sacrum. A bore extends through the elongate trunk. A longitudinal axis may be defined between the proximal and distal ends, and a periphery may be defined by an outer surface of the elongate trunk. The implant further comprises a proximal anchor comprising at least one deformable feature. The deformable feature is adapted to move between an initial configuration in which the deformable feature is within the periphery of the elongate trunk, and a deployed configuration in which at least a portion of the deformable feature extends outwardly beyond the periphery of the elongate trunk relative to the longitudinal axis to engage the ilium. Additionally, the implant comprises a distal anchor coupled to the elongate trunk. The distal anchor comprising an expandable member defining an interior in fluid communication with the bore of the elongate trunk. The expandable member is adapted to receive curable material to move between a collapsed state in which the expandable member is within the periphery of the elongate trunk, and an expanded state in which at least a portion of the expandable member extends outwardly beyond the periphery of the elongate trunk relative to the longitudinal axis to engage the sacrum.

According to certain aspects of the present disclosure, the implant comprises a stem extending proximally from the proximal end of the elongate trunk. The stem comprises driven features configured to engage complimentary drive features of an insertion tool. The proximal anchor comprises engagement features coupled to the elongate trunk and configured to engage complimentary engagement features of the insertion tool. The deformable features may be circumferentially arranged about the outer surface of the elongate trunk. The deformable features are adapted to buckle in response to compressive loads applied to the proximal anchor such that at least a portion of the deformable features extend beyond the periphery of the elongate trunk relative to the longitudinal axis to engage the ilium.

According to certain aspects of the present disclosure, the minimally invasive bone stabilization system includes the insertion tool comprising a driver configured to receive a rotational input, a first shaft comprising a distal end and engagement features at the distal end, a second shaft coaxially arranged within the first shaft. The second shaft includes a proximal end coupled to the driver, a distal end opposite the proximal end, drive features near the distal end, and a lumen extending through the second shaft.

A method for preventing relative motion between the ilium and the sacrum with the implant is also disclosed. The method comprises the steps of creating a minimally invasive incision within skin. An access cannula is positioned through the minimally invasive incision. A borehole is resected through the ilium and into the sacrum through the access cannula. The implant is positioned within the borehole such that the proximal anchor is disposed in the ilium and the distal anchor is disposed in the sacrum. The insertion tool removably coupled to the implant is operated to apply a compressive force to the proximal anchor along the longitudinal axis. The proximal anchor moves from the initial configuration in which the proximal anchor is within the periphery of the elongate trunk, to the deployed configuration in which at least a portion of the deformable feature of the proximal anchor extends outwardly beyond the periphery of the elongate trunk relative to the longitudinal axis to engage the ilium. Curable material is injected through the bore and into the expandable member to move the expandable member between the collapsed state in which the expandable member is within the periphery of the elongate trunk, and the expanded state in which at least a portion of the expandable member extends outwardly beyond the periphery of the elongate trunk relative to the longitudinal axis to engage the sacrum

BRIEF DESCRIPTION OF THE DRAWINGS

The disclosure is pointed out with particularity in the claims. The above and further features and benefits of the disclosure are understood by the following Detailed Description taken in conjunction with the accompanying drawings.

FIG. 8 is a perspective view of the implant of FIG. 1 with the proximal anchor in the deployed configuration and the distal anchor in the expanded state.

FIG. 9 is a cross sectional view of the implant of FIG. 8 with the proximal anchor in the deployed configuration within the first tissue section and the distal anchor in the expanded state within the second tissue section.

DETAILED DESCRIPTION

Figure 1:
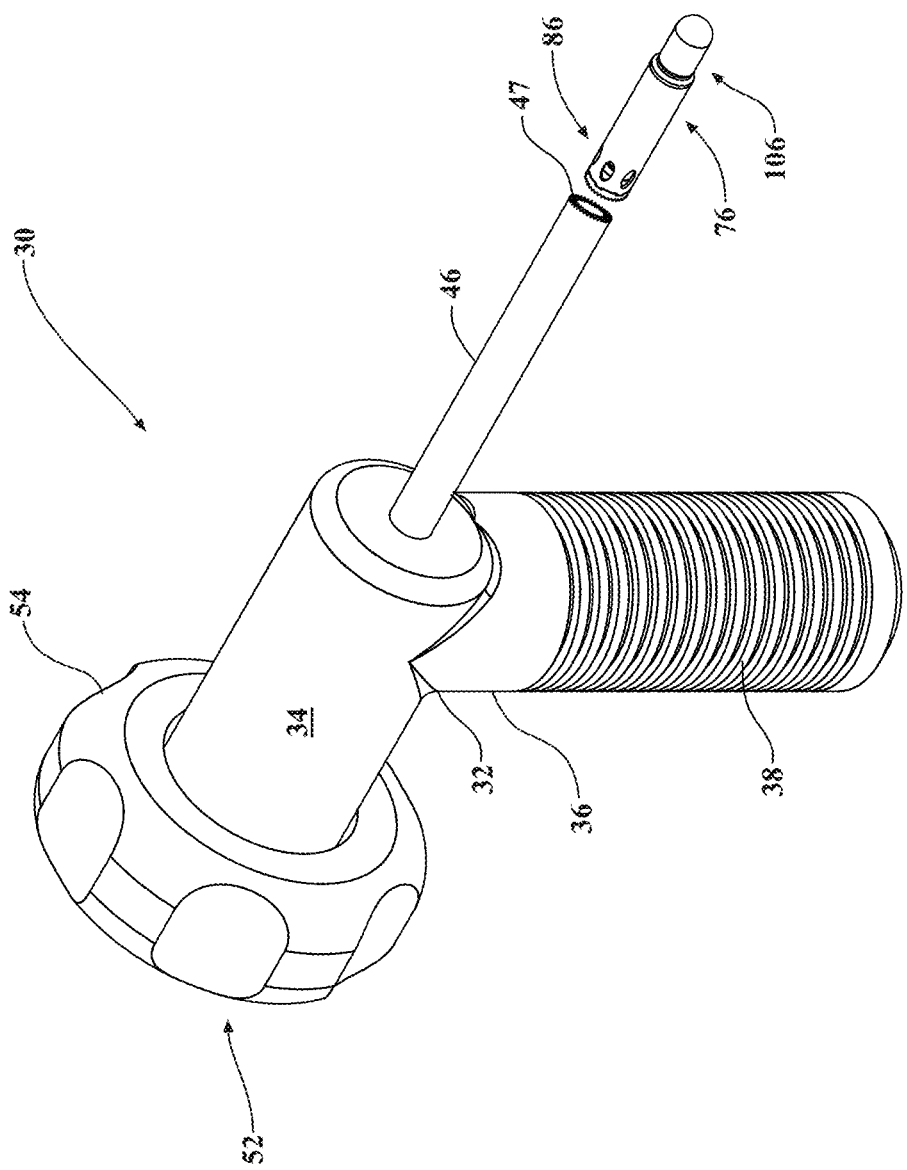
FIG. 1 is a perspective view of an implant and an insertion tool.

FIG. 1 depicts an insertion tool 30 and an implant 76 for a minimally invasive stabilization system. The implant 76 is configured to be inserted into a patient to hold two sections of tissue together. FIGS. 7, 9 and 13A-13C, for example, show a first tissue section 122 and a second tissue section 124 separated by an interface 326 or joint space. The first and second tissue sections 122, 124 may be a first and second bone, respectively. In one example to be described throughout the present disclosure, the first tissue section 122 is an ilium, the second tissue section 124 is a sacrum, and the interface 326 may generally define the SI joint. It is to be understood that the implant 76 may be used with other surgical procedures to prevent relative motion of patient anatomy, for example, spinal fusion, ankle fusion, foot fusion, wrist fusion, hand fusion, fracture fixation, dislocation reduction, and the like. In a manner to be described in more detail, the implant 76 is removably coupled to the tool 30. The tool 30 is operated by a user to position and deploy the implant 76 to prevent relative motion between the sacrum and the ilium.

The implant 76, best shown in FIGS. 2, 3A, 3B and 8, includes an elongate trunk 90. The trunk 90 is defined between a proximal end 302 configured to be positioned within the first tissue section 122 and a distal end 304 configured to be positioned within the second tissue section 124. The trunk 90 extends between the first tissue section 122 and the second tissue section 124. A proximal anchor 86 is located proximally from the proximal end 302 of trunk 90, and a distal anchor 106 is located distally to the distal end 304 of the trunk 90. ("Proximal" is understood to mean towards the practitioner, away from the site in which the implant 76 is to be seated; and "distal" is understood to mean away from the practitioner holding the tool 30, towards the site in which the implant 76 is to be seated.) In a manner to be described, the tool 30 is used to deploy the proximal anchor 86, and in certain embodiments the distal anchor 106. Once the proximal and distal anchors 86, 106 are deployed, the implant 76 secures the first and second tissue sections 122, 124.

The implant 76 is shaped so that trunk 90 is elongate in shape. The trunk 90 includes a periphery 306 defined by an outer surface 308 of the trunk 90. In the illustrated embodiment, the trunk 90 is cylindrical and has a length defined between the proximal and distal ends 302, 304 and a diameter defined by the periphery 306. In other words, FIG. 3A shows the outer surface 308 extending circumferentially to define the periphery 306. The proximal anchor 86 may be a tubular shaped structure that extends proximally from the proximal end 302 of trunk 90. In the illustrated embodiment, at least a portion of the proximal anchor 86 is formed integrally with the trunk 90. The proximal anchor 86 comprises at least one deformable feature 310 that is, at least initially, within the periphery 306 of the trunk 90. In certain embodiments, the implant 76 is shaped so that the outer diameter of proximal anchor 86 and the periphery 306 of the trunk 90 are initially equal. The deformable feature 310 of the proximal anchor 86 is adapted to move between an initial configuration (shown in FIGS. 2 and 3) in which the deformable feature 310 is within the periphery 306 of the trunk 90, and a deployed configuration (shown in FIGS. 8 and 9) in which at least a portion of the deformable feature 310 extends outwardly beyond the periphery 306 relative to the longitudinal axis 300 to engage the first tissue section 122, e.g., the ilium. The distal anchor 106 is coupled to the trunk 90 and comprises an expandable member 312. The expandable member 312 is adapted to receive injectable material to move between a collapsed state (shown in FIGS. 6 and 7) in which the expandable member 312 is within the periphery 306 of the trunk 90, and an expanded state (shown in FIGS. 8 and 9) in which at least a portion of the expandable member 312 extends outwardly beyond the periphery 306 of the trunk 90 relative to the longitudinal axis 300 to engage the second tissue section 124; e.g., the sacrum. Thus, prior to positioning the implant 76 within the patient, the proximal and distal anchors 86, 106 are within the periphery 306 to minimize the axial profile of the implant 76 and facilitate surgery that is less or minimally invasive. Relative to known system with diameters of 10, 12 or greater millimeters (mm) (and/or requiring the use of a tissue dilator), the implant 76 of the present disclosure advantageously has smaller diameters that provides for percutaneous placement through a minimally invasive incision. Exemplary diameters of the implant 76 include less than 10 mm, and more particularly less than 7 mm, and even more particularly less than 4 mm. Further, the component of tool 30 used to position the implant 76 need not require a diameter larger than that of the implant 76 itself. Consequently, the relatively smaller incision and borehole exposes the patient to less trauma.

As used herein, injectable material may include any material suitable for injection into the patient for use with the stabilization system and/or as part of the methods disclosed herein. The injectable material may include a curable material, for example, a biocompatible curable material (bone cement). Exemplary curable materials include non-resorbable curable materials such as polymethylmethacrylate (PMMA) or glass ionomer cements, or resorbable material such as calcium phosphate. The injectable material may include a bone growth material (e.g., autograft bone, allograph bone, and/or synthetic material that fosters bone growth). The injectable material may include therapeutic agents, for example, a pharmacologic that reduces infection or tissue inflammation). Other injectable materials suitable with the present system and methods are contemplated, and it is also understood that combinations of the aforementioned injectable materials may be utilized (e.g., calcium phosphate with demineralized bone matrix and bioglass). In alternative embodiments, the material received within the interior 314 of the expandable member 312 is not injected, but rather packed with a tamp or otherwise provided in a suitable manner.

Figure 3A:
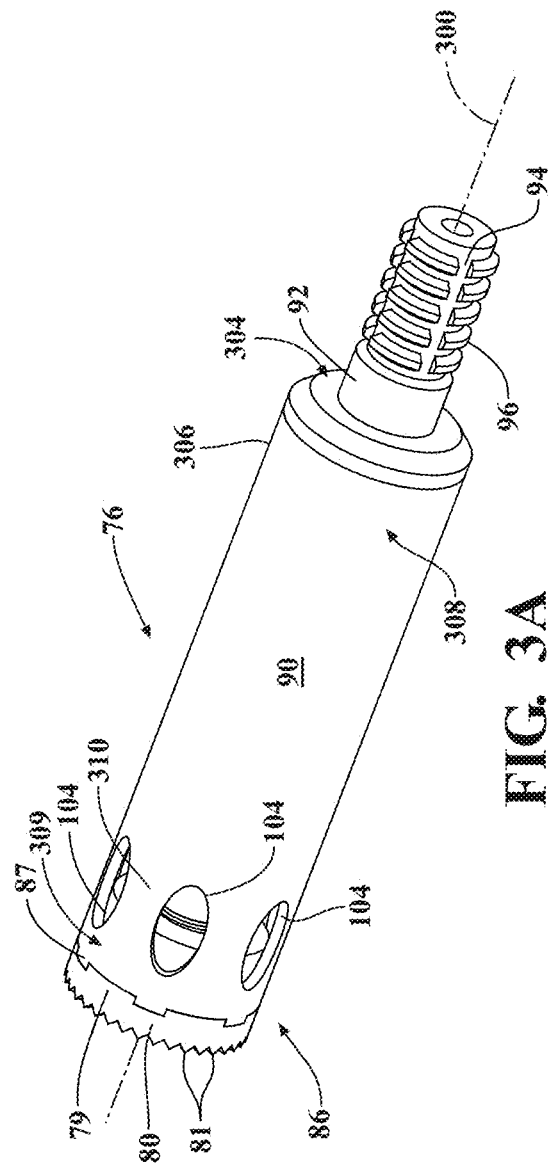
FIG. 3A is a perspective view of the implant of FIG. 1 with an expandable member forming a portion of a distal anchor removed.
Figure 3B:
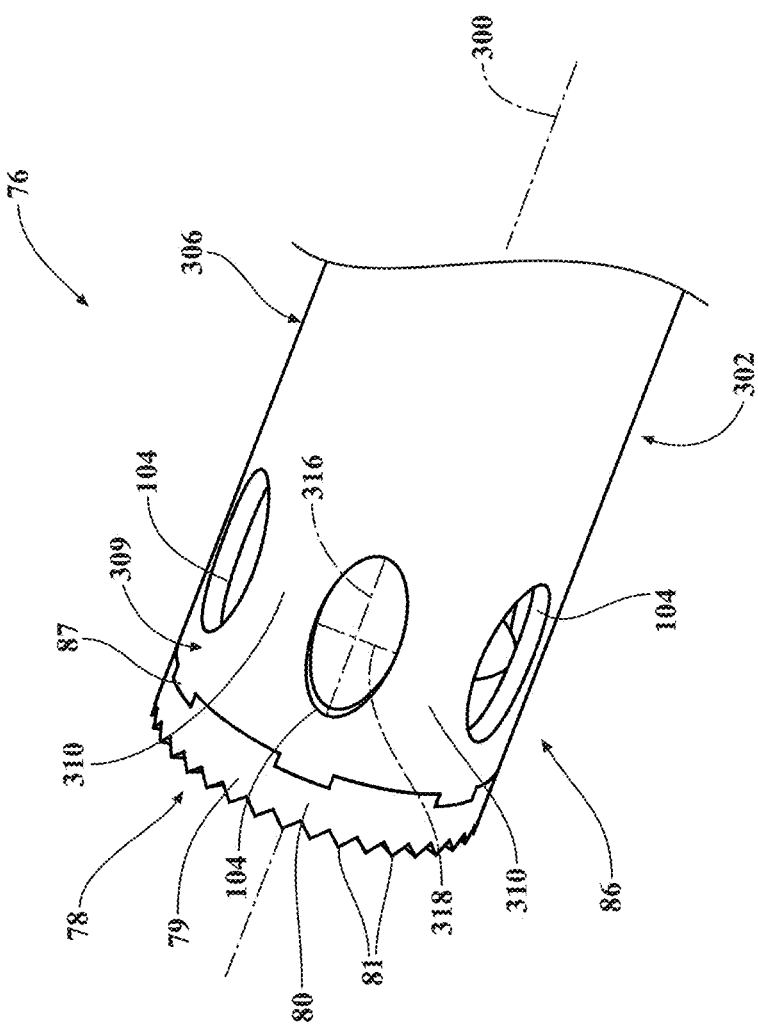
FIG. 3B is a partial perspective view of the implant of FIG. 1 showing a proximal anchor.

With reference to FIGS. 3A and 3B, the proximal anchor 86 includes a plurality of apertures 104. The apertures 104 extend through the anchor 86, and may be circumferentially arranged and arcuately spaced apart from each other on an outer surface 309 of the proximal anchor 86 integrally formed with the outer surface 308 of the trunk 90. In other words, the outer surfaces 308, 309 may be a singular, continuous structure, as shown, but are separately identified to delineate the portion of the outer surface defining the proximal anchor 86. The apertures 104 define a deformable feature 310 interposed between each adjacent pair of apertures 104. Each of the apertures 104 may be oval in shape and comprise a major axis 316 and a minor axis 318. The implant 76 is formed so that the major axes 316 of apertures 104 are parallel to the longitudinal axis 300 through the implant 76, as shown in FIG. 3B. In a manner to be described, the apertures 104 are configured to localize stresses to the deformable feature 310 from compressive loads applied to the proximal anchor 86 to induce deformation of the deformable feature 310 and move the deformable feature 310 from the initial configuration to the deployed configuration. Each of the deformable features define a width, where the width is smallest at a position between the minor axes 318 of adjacent pairs of apertures 104 such that the localized stresses induce buckling to the deformable features 310 at the widths. In another exemplary embodiment, a plurality of slots (not shown) may be circumferentially arranged and spaced apart from each other on the outer surface 309 of the proximal anchor 86. The slots define the deformable feature 310 interposed between each adjacent pair of the slots with the deformable feature 310 being strut-like in shape. The localized stresses induce bowing of the struts with each of the bowed struts including an apex in the deployed configuration with the apex extending beyond the periphery 306 of the trunk 90 relative to the longitudinal axis 300. In still another exemplary embodiment, the proximal anchor 86 may take the appearance of an annular cage in at least some respects similar to a cardiovascular stent. The annular cage include a grid-like pattern of structural members (i.e., the deformable features 310) with interstitial spaces (i.e., the apertures 104). The cage is configured to deform, deflect, buckle, bow, and/or otherwise deform in response to the compressive loads applied to the proximal anchor 86 such that at least a portion of the cage extends beyond the periphery 306 of the trunk 90 relative to the longitudinal axis 300.

For still another example, the proximal anchor 86 may include opposing wings configured to deflect outwardly in response to the screw-like member being axially advanced on contact with the opposing wings. It is to be understood that deformation may include deflection of at least a portion of the proximal anchor 86. For still yet another example, the proximal anchor 86 may include a scissor-like jack having two opposing surfaces configured to move in opposite directions in response to the screw-like member being axially advanced.

The proximal end of proximal anchor 86 may be castellated. Specifically plural arcuately spaced apart tabs 87, as shown in FIGS. 3A and 3B, extend proximally from the proximal end of the proximal anchor 86. A cap 78 is disposed over the proximal end of proximal anchor 86. The cap 78 is formed to have a base 79. The base 79 is formed with slots 80 that extend inwardly from a distally directed face of the base 79. The slots 80 are dimensioned to receive the tabs 87 defining the castellated proximal end of the proximal anchor 86. The seating of the tabs 87 in the slots 80 prevents relative rotation of cap 78 and the trunk 90. The cap 78 may include cylindrically shaped skirt 82. The skirt 82 extends distally forward from an inner perimeter of the base 79. The skirt 82 defines a circular void space or cavity 320 for purposes to be described. The cap 78 is further formed so the proximal end of the base 79 is formed to have an engagement feature, such as teeth 81 identified in FIGS. 3A and 3B, adapted to receive a complimentary engagement feature, such as complimentary teeth of the tool 30 (see FIG. 6). The cap 78 includes a lid 83, identified only in FIG. 2, extending over the top of skirt 82 to define an aperture (not identified).

Figure 2:
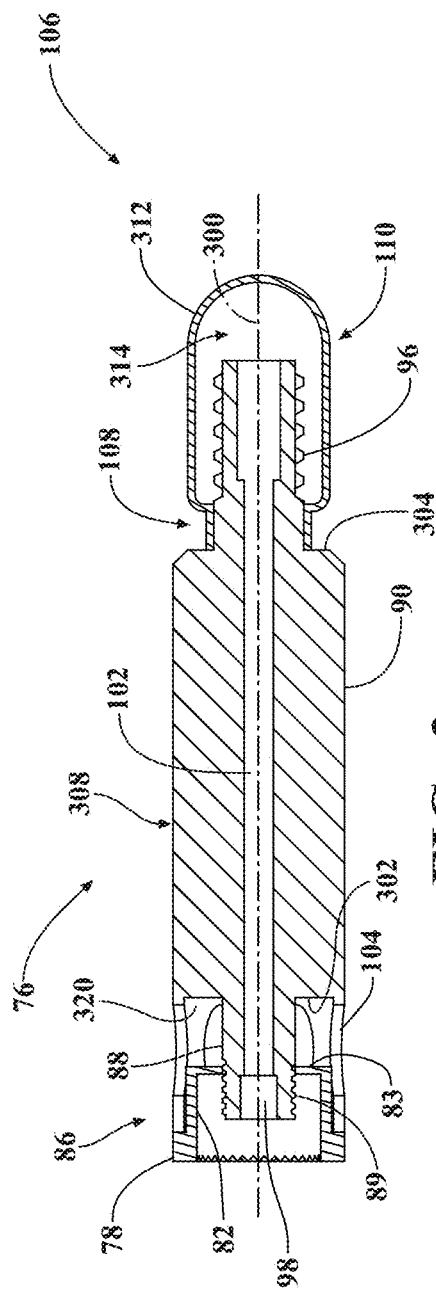
FIG. 2 is a cross sectional view of the implant of FIG. 1.

With reference to FIG. 2, the implant 76 also includes a stem 88. The stem 88, like the proximal anchor 86, extends proximally from the proximal end 302 of the trunk 90. A diameter of the stem 88 is less than the diameter of the trunk 90 such that the stem 88 may be disposed in the void space 320 internal to the proximal anchor 86 and within the skirt 82 of the cap 78. The stem 88 may extend through the aperture of the lid 83 of the cap 78. The stem 88 may be centered on a longitudinal axis 300 of the trunk 90. In the illustrated embodiment, a proximal end of the stem 88 is located distally forward of the proximal end of proximal anchor 86. The stem 88 is formed so that a driven feature, such as threads 89, extends around the outer surface of the stem 88. The driven feature is configure to engage a drive feature, such as complimentary threading 64, of the tool 30.

Turning to the distal anchor 106 of the implant 76, a neck 92 extends distally forward from the distal end 304 of the trunk 90. Referring to FIGS. 2, 3A and 3B, the neck 92 may be cylindrical in shape and comprises a diameter less than the diameter of the trunk 90 and separated by a distally directed step surface defining the distal end 304 of the trunk 90. The implant 76 may include a head 94 distal to the neck 92. The head 94 may be cylindrical in shape and centered on the longitudinal axis 300. A gripping feature is coupled to the neck 92 in order to facilitate axial retention of the implant 76 in the sacrum 124. One example of the gripping feature is ribs 96, one each identified in FIGS. 2 and 3, which are coupled to and extend radially outwardly from the neck 92. The ribs 96 extend arcuately around the outer surface of the neck 92. In the illustrated embodiment, implant 76 is formed to have plural ribs 96 longitudinally spaced apart from each other along the head 94. In the illustrated embodiment, the implant 76 may be formed so that multiple ribs 96 may be spaced axially from each other such that the ribs 96 form multiple rows. The ends of these ribs 96 are angularly spaced apart from each other. The ribs 96 may have an outer diameter approximately equal to the outer diameter of the neck 92. Alternative gripping features may be used instead of or in combination with the rib 96. For example, the gripping feature may include a porous surface, a coating, a knurled surface, a circumferential groove, threads, a roughened surface of neck 92 and the head 94, and an anchor similar to the proximal anchor. The gripping features provide enhanced axial retention between the implant 76 and the curable material to be cured about the head 94 in a manner to be described.

Figure 6:
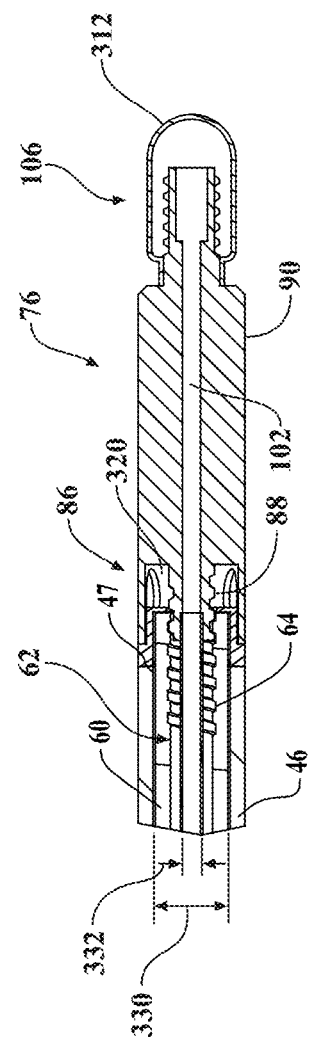
FIG. 6 is an enlarged cross sectional view showing the implant secured to a distal end of the insertion tool.
Figure 7:
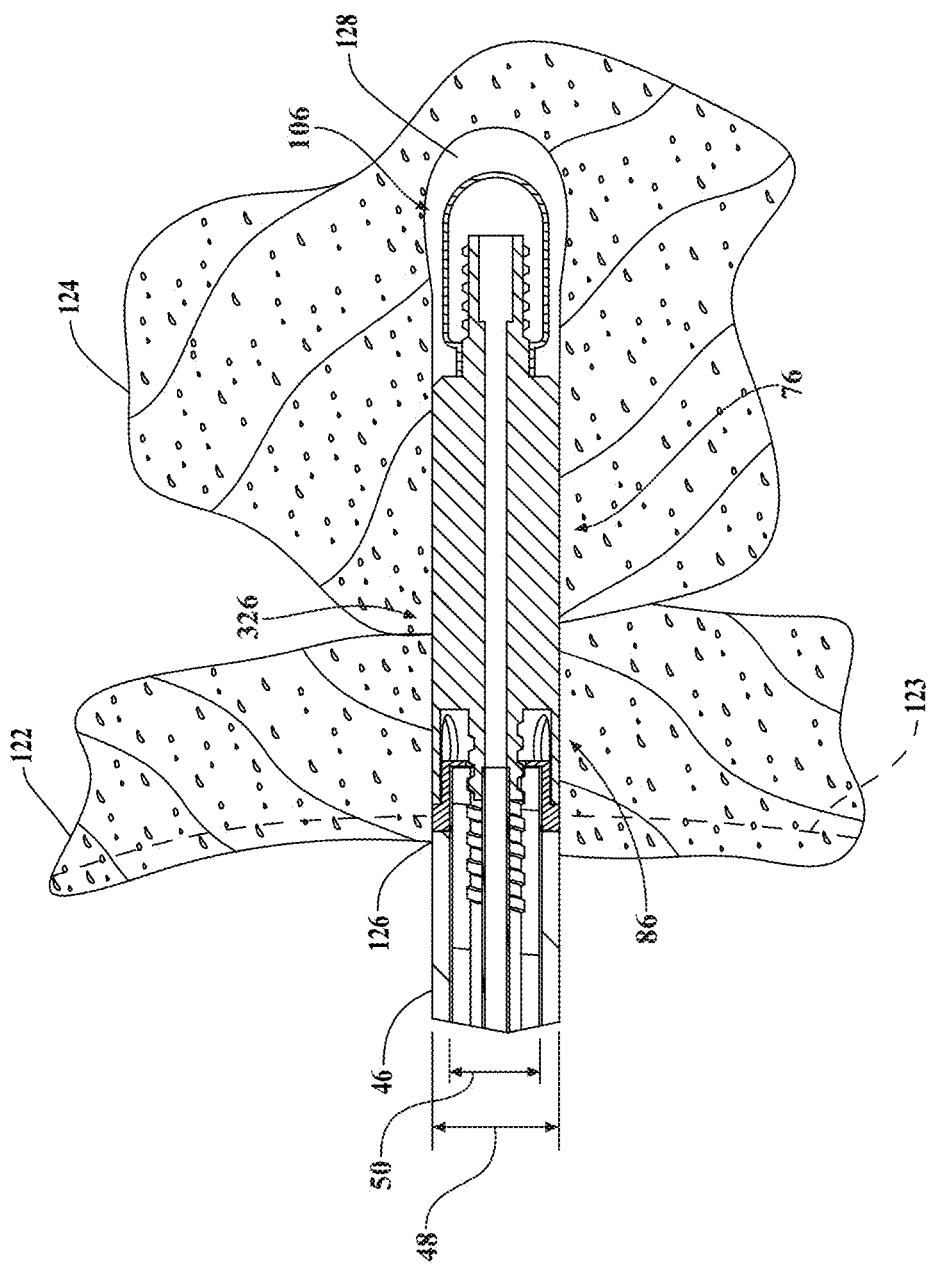
FIG. 7 is a cross sectional view of the implant and the insertion tool of FIG. 6 with the implant positioned within first and second tissue sections. The proximal anchor is in the initial configuration and the distal anchor is in the collapsed state.

With reference to FIGS. 2 and 6, the implant 76 is also formed to have a bore 102 that extends proximally to distally along the longitudinal axis 300 of the implant 76. The bore 102 may be in communication with a coaxial counterbore 98 extending distally forward from a proximal end of stem 88 to a distal end of the stem 88 (e.g., the proximal end 302 of the trunk 90). The counterbore 98 is understood to be larger in diameter than bore 102. The bore 102 extends from through the trunk 90, through the neck 92 and head to an opening in the head 94.

The distal anchor 106 is coupled to the trunk 90 and comprises an expandable member 312 that defines an interior 314 in fluid communication with the bore 102 of the trunk 90. The expandable member 312 is coupled to the neck 92 such that the head 94 and each rib 96 is located within the interior 314 of the expandable member 312. For example, the expandable member 312 may be a flexible, inflatable balloon. In some versions of the disclosure, the expandable member 312 is formed from a thermoplastic polyurethane or other elastomeric material. The expandable member 312 is shaped to have a narrowed portion 108, identified only in FIG. 9. The narrowed portion 108 is shaped to tightly fit around neck 92. An adhesive, clamp, or other joining means may be used to hold the narrowed portion 108 fast to the neck 92. Distal to the narrowed portion 108, the expandable member 312 is shaped to have an expanding portion 110, identified in FIGS. 2, 10 and 11. The expanding portion 110 of the expandable member 312 extends over and around head 94 such that the head 94 of the implant 76 (and the ribs 96) are disposed within the interior 314 of the expandable member 312. The distal end of bore 102 opens into the interior 314 defined by the distal anchor 106 to receive the injectable material in a manner to be described.

Figure 4:
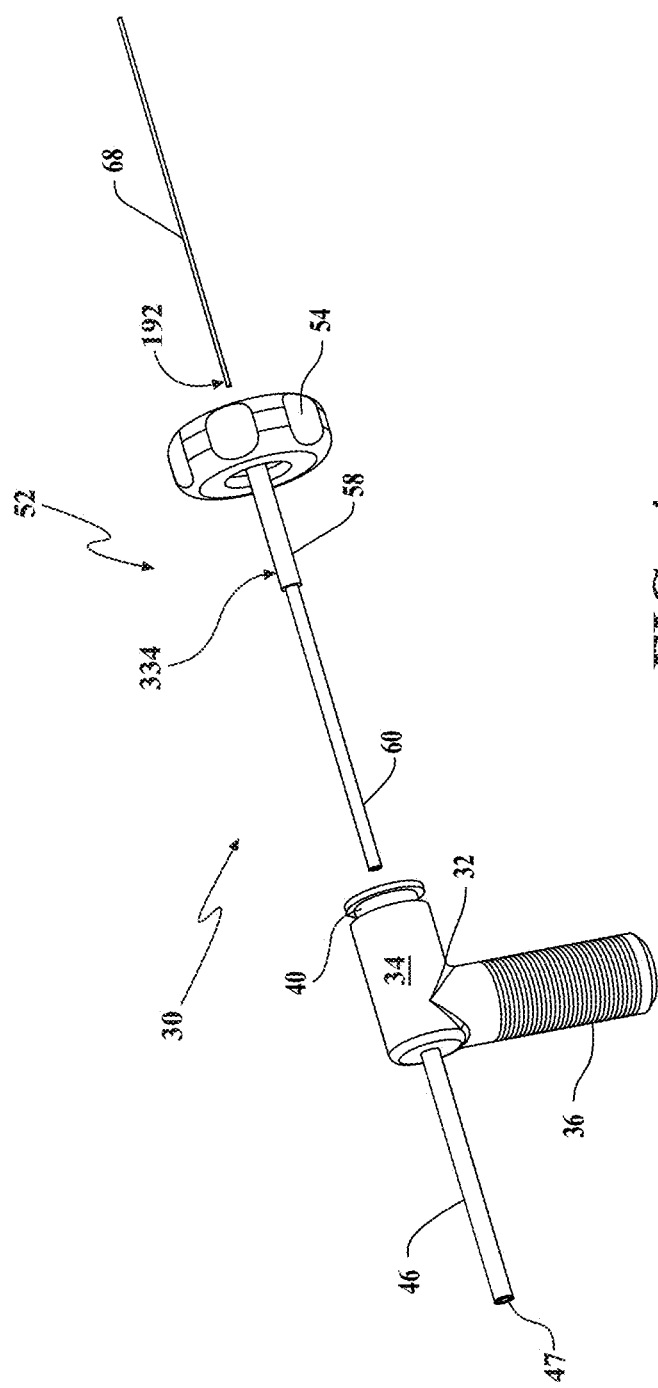
FIG. 4 is an exploded view of the insertion tool of FIG. 1 with a delivery cannula configured to be positioned within a lumen of the insertion tool.
Figure 5:
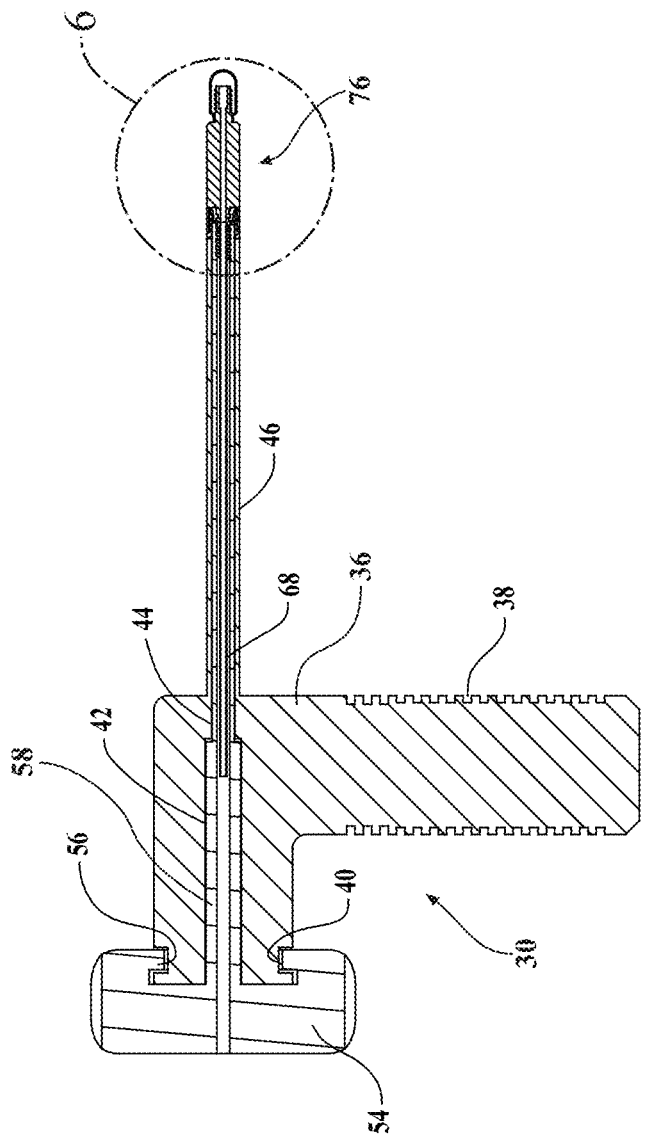
FIG. 5 is a cross sectional view of the implant and the insertion tool of FIG. 1.

Returning to FIG. 1 and with concurrent reference to FIGS. 4-6, the tool 30 includes a handle 32, sometimes called a housing. The handle 32 is shaped to have a barrel 34. In the illustrated embodiment, barrel 34 is cylindrically shaped. A handgrip 36, also part of the handle 32, extends outward from the barrel 34 adjacent the distal end of the barrel 34 to form a "pistol grip." In the illustrated embodiment, the handgrip 36 is cylindrical in shape. Plural longitudinally spaced apart grooves 38 extend circumferentially around the outer curved surface of the handle. The grooves 38 facilitate the grasping of the handle 32.

The barrel 34 is formed so that immediately forward of the proximal end there is a slot 40. The slot 40 extends inwardly from and circumferentially around the outer surface of the barrel 34. The handle 32 is further formed so two coaxial bores extend between the opposed proximal and distal end of the barrel 34. A first bore, bore 42, extends distally forward from the proximal end of the barrel 34. The bore 42 extends a length that is between 40% and 80% of the overall length of the barrel 34. A second bore, bore 44, extends forward from the distal end of bore 42 to the distal end of the barrel 34. The bore 44 has a diameter that is less than the diameter of bore 42. The bores 42 and 44 are centered on the proximal to distal longitudinal axis 300 through the barrel 34.

A first shaft 46 extends distally forward of the distal front end of the barrel 34 and is defined by an outer diameter 48. The bore 44 extends through the shaft 46 and is defined by an inner diameter 50. The inner diameter 50 and outer diameter 48 may be approximately equal to, if not identical to the inner and outer diameters of the base 79 of the cap 78. The distal end of the shaft 46 is formed to have a complementary engagement feature, such as teeth 47, identified in FIGS. 1 and 6. The teeth 47 are shaped to engage cap teeth 81. The shaft 46 may be integrally formed with the barrel 34, or a separate component that is secured to the barrel 34.

A driver 52 is rotatably mounted to the handle 32. The driver 52 includes a knob 54. The knob 54 is rotatably mounted around the proximal end of the barrel 34. Shown in FIG. 5, the driver 52 includes an inwardly-directed lip 56. The handle 32 is assembled so that the lip 56 seats in, and is able to rotate in, the slot 40 formed in the barrel 34. The driver 52 is able to rotate within, but not move longitudinally relative to, the barrel 34. The driver 52 comprises a drive shaft 60 (also referred to herein as a second shaft) integral with and extending distally forward from the knob 54 along the longitudinal axis 300. The drive shaft 60 has an outer diameter 330 that is less than an inner diameter 50 of the shaft 46. The drive shaft 60 includes a shoulder portion 58 that extends distally forward from the distally directed face of the knob 54. The shoulder portion 58 is shaped to closely slip fit and rotate in the bore 42 and has a diameter 334 larger than the outer diameter 330. The drive shaft 60, which is smaller in outer diameter than the shoulder portion 58, is shaped to closely slip fit and rotate in both the barrel 34 and the shaft 46. The components forming the handle 32 are further constructed so that the distal end of the drive shaft 60 is located forward of a distal end of the first shaft 46. A lumen 62, identified in FIG. 6, extends longitudinally through the driver 52 and has a diameter 332. The lumen 62 extends from the proximally directed face of the knob 54, through the drive shaft 60 to the distal end of the drive shaft 60.

Figure 18:
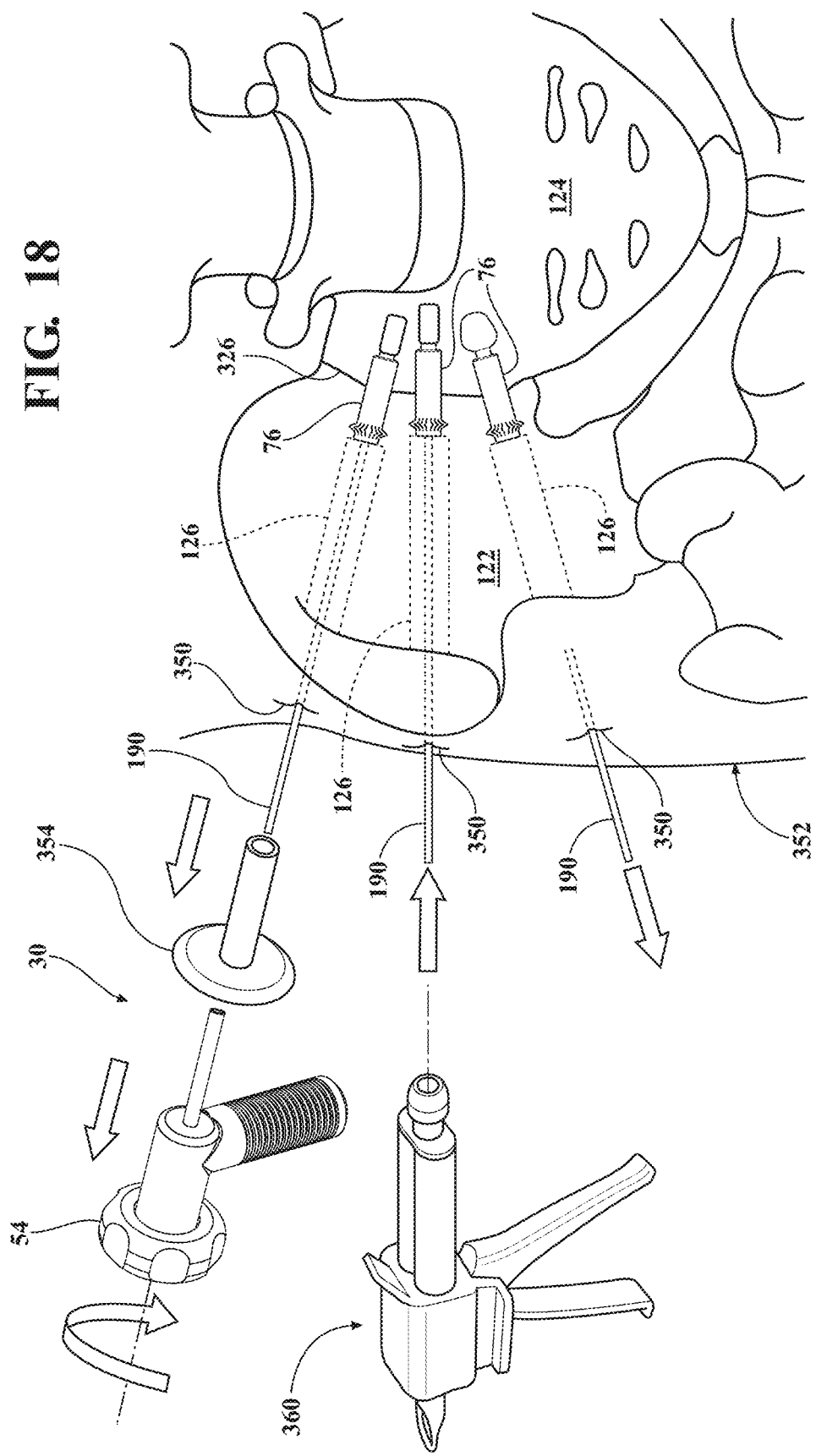
FIG. 18 is a schematic view of a sacroiliac joint of a patient with a plurality of implants positioned within the SI joint and each of the implants depicting a different step of an exemplary method for fixing the ilium and sacrum.

The driver 52 is further formed so immediately rearward of the open distal end of the drive shaft 60, there is a drive feature, such as threading 64, around the inner wall of the driver 52 that defines the lumen 62. The driver 52 is dimensioned so the distal end of the drive shaft 60 can seat in the annular space within the cap skirt 82, the lumen 62 can seat over the stem 88 and threading 64 can engage the threading 89. The driver 52 is further formed so a delivery cannula 68, seen in FIGS. 4 and 5, can be slidably disposed in the lumen 62. The system is further dimensioned so a distal end of the delivery cannula 68 is sized to be seated in the counterbore 98 internal to the implant 76, for example, through an interference fit. In some embodiments, such as shown in FIG. 18, the delivery cannula 68 has a length defined between opposing ends with the length being such that when the implant 76 is positioned within the borehole 126 the delivery cannula 68 extends above the skin 352 of the patient. The delivery cannula 68 may be used to verify the placement of the implant 76, and/or to inject the injectable material, discussed in further detail below.

To prepare tissue for receiving implant 76 of this disclosure, the first and second tissue sections 122, 124 are aligned. A dashed line 123 marks the approximate boundary between the outer relatively hard outer layer of cortical bone and softer internal layer of cancellous bone of the tissue or bone section 122 (it is also understood the second tissue section may also include cortical and cancellous bone). Once the first and second tissue sections 122, 124 are aligned, an incision may be provided within the overlying tissue (e.g., skin, fascia and muscle), and the overlying tissue may be dilated with a suitable instrument to provide a working channel to the first tissue section 122. A borehole 126 is formed through at least a portion of the first and second tissue sections 122, 124. The borehole 126 may be formed so as to have an overall length that is greater than the length of the implant. More particularly, the borehole 126 may be formed so as to have a length such that when the proximal anchor 86 is deployed, the proximal anchor 86 may be deployed within the portion of the cancellous bone adjacent the cortical bone. A closed distal end of the borehole 126 may be cored so as to create a cavity 128, for example, slightly larger than the diameter of the borehole 126. A cavity creator such as an expandable balloon tamp or a blade type cavity creator such as disclosed in PCT Pub. No. WO 2010/017377/US Pat. Pub. No. US 2010/0036381, the contents of which are explicitly incorporated herein may be used to form the borehole 126.

In certain embodiments, a guidewire (not shown) may be provided to facilitate creation of the borehole 126. An access cannula 354 with an access needle 356 (see FIG. 14) disposed within the access cannula 354 are directed through the incision 350 and the overlying tissue to dilate the overlying tissue. The access needle 356 prevents coring of the overlying tissue within the access cannula 354 as the access cannula 354 and the access needle 356 are directed through the overlying tissue. The access needle 356 (e.g., a trocar) is removed to provide the working channel through the overlying tissue to the first tissue section 122. The guidewire is directed through the working channel and into engagement with the first tissue section 122. The access cannula 354 may be removed with the guidewire remaining in engagement with the first tissue section 122 and extending above the skin 352 of the patient.

The borehole 126 is then formed through at least a portion of the first and second tissue sections 122, 124. In particular, a drill 358 (see FIG. 15) is cannulated so as to slidably receive the guidewire. The drill 358 is directed through the incision 350 and the overlying tissue while constrained by the guidewire. The drill 358 is actuated (e.g., rotated under manual or powered input) to create the borehole 126. The drill 358 is removed with the guidewire remaining in engagement with the first tissue section 122 and extending above the skin 352 of the patient.

The implant 76 is removably coupled to the tool 30. In particular, the distal end of the drive shaft 60 of the tool 30 is positioned within the skirt 82 integral of the implant 76. The knob 54 is rotated to cause the like rotation of drive shaft 60. The rotation of the drive shaft 60 causes the threading 64 to engage the threading 89 coupled to the stem 88. The implant 76 is threaded onto drive shaft 60 until the teeth 81 of the cap 78 engage the complementary teeth 47 integral with tool 30, as seen in FIGS. 5 and 6. The engagement of teeth 47 with the teeth 81 prevent the implant 76 from rotating relative to tool shaft 46.

The delivery cannula 68 may be inserted into the lumen 62. The delivery cannula 68 is optionally preloaded loaded with the injectable material. The cannula 68 is fitted in the lumen 62 so the distal end of the cannula 68 seats in counterbore 98 internal to the implant 76.

The tool 30 is used to position the implant 76 within the borehole 126. In certain embodiments, the tool 30 directs the implant 76 through the access cannula 354 and into the borehole 126. The implant 76 may be positioned such that the proximal anchor 86 is located inward of the boundary 123 between the cortical and cancellous layers of the first tissue section 122, and distal anchor 106 is located in the second tissue section 124, for example, within the cavity 128. In embodiments utilizing the guidewire (with the access cannula 354 removed), the tool 30 and the implant 76 are cannulated so as to slidably receive the guidewire. The tool 30 and the implant 76 are directed through the incision 350 and the overlying tissue while constrained by the guidewire.

The proximal anchor 86 is deployed by actuating the driver 52. The driver 52 is actuated by rotating knob 54, and the rotation of knob 54 results in a like rotation of drive shaft 60. It is understood that, at this time, implant 76 is blocked from rotation relative to tool 30, and the stem 88 is threadably engaging the drive shaft 60. Accordingly, the rotation of drive shaft 60 draws the stem 88 proximally and, by extension, an entirety of the implant 76 moves proximally relative to the tool 30. With movement of the cap 78 blocked by the abutment of the cap 78 against the distal end of shaft 46, the proximal anchor 86 is compressed between cap 78 and trunk 90 of the implant 76. Owing to the presence of apertures 104 localizing compressive stresses, the deformable features 310 of the proximal anchor 86 is relatively mechanically weak. In other words, in response to longitudinally compressive forces, the deformable features 310 of the proximal anchor 86, in comparison to other sections of the implant 76, are less able to resist buckling. Accordingly, in response to the longitudinally compressive force placed on anchor 86, the deformable features 310 buckle outwardly. The deformable features 310 are adapted to buckle into two buckled sections separated by an elbow that projects radially outwardly beyond the periphery 306 of trunk 90, as seen in FIGS. 8 and 9. As a result of this buckling, the buckled sections and the elbow of the anchor 86 penetrate into the first tissue section 122 surrounding borehole 126. The penetration of the deployed anchor 86 into the surrounding tissue prevents movement of the implant 76 relative to the first tissue section 122.

The distal anchor 106 is deployed. It is understood the deploying of the distal anchor 106 may occur before or after deploying of the proximal anchor 86. The deploying of the distal anchor 106 may include expanding the expandable member 312 with the injectable material. In one example, a stylet (not shown) is inserted into the lumen 62 to urge the injectable material preloaded into the delivery cannula 68 to flow through bore 102 internal to the implant 76 and into the expandable member 312. The injectable material is discharged from the open end of bore 102 in into the interior 314 of the expandable member 312. The injectable material expands the expandable member 312 from the collapsed state from which the expandable member 312 is within the periphery 306 of the trunk 90, the expanded state in which at least a portion of the expandable member 312 extend outwardly beyond the periphery 306 of the trunk 90 relative to the longitudinal axis 300. The expandable member 312 contacts and engages the second tissue section 124. The expandable member 312 may compress the surrounding tissue against which the expandable member 312. In embodiments utilizing the guidewire (with the access cannula 354 removed), the distal anchor 106 cannulated so as to slidably receive the guidewire. For example, the expandable member 312 of the distal anchor 106 may be, for example, a torus or toroid defining an inner passageway through the expandable member 312. A suitable structure may be coupled to the implant 76 to axially support the toroidal expandable member at its distal end. For example, the neck 92 (or an additional neck) may extend through substantially an entirely of a length of the toroidal expandable member. In such an example, the inner passageway is sized to slidably receive the guidewire such that, as the tool 30 and the implant 76 are directed through the incision 350, the guidewire is disposed within the inner passageway of the expandable member 312 prior to injecting the injectable material into the interior 314 of the expandable member 312.

In embodiments where the injectable material is curable material, the curable material may be permitted to cure or harden, resulting in a mass 130 of cured material, shown in FIG. 9, extending outwardly from and around the head 94 of the implant 76. Further, the curable material hardens around the ribs 96 integral with head 94 and neck 92. The hardening of the curable material around the ribs 96 reduces the likelihood that, should the implant 76 and tissue section 124 be subjected to axial loads, the implant 76 will work free from the hardened mass 130 (e.g., "pull out"). The mass 130 and the expandable member 312 prevent movement of the implant 76 relative to the second tissue section 124. When the proximal and distal anchors 86 and 106 engaging the first and second tissue sections 122, 124, respectively, relative movement between the tissue sections 122, 124 is prevented.

Once the implant 76 is deployed, driver 52 is actuated to disconnect the tool 30 from the implant 76. The knob 54 is rotated in the direction opposite the direction in which the knob 54 is rotated to deploy the proximal anchor 86. At this time, the proximal and distal anchors 86, 106 constrain the implant 76 from movement relative to the tissue sections 122, 124. Accordingly, as a result of the rotation of drive shaft 60, the drive shaft 60 rotates proximally away from the stem 88. Since the drive shaft 60 does not move longitudinally relative to the rest of the tool 30, the proximal movement of the tool 30 separates the tool from the implant 76. Subsequent steps of exemplary procedures will be described in further detail.

Figure 10:
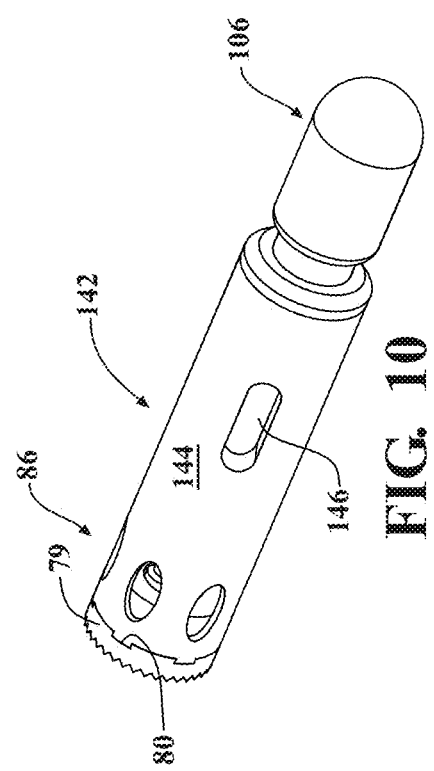
FIG. 10 is a perspective view of an implant in accordance with another exemplary embodiment of the present disclosure.

Referring now to FIG. 10, an implant 142 in accordance with another exemplary embodiment is shown. In at least many respects the implant 142 of the present embodiment is the same as that previously described. The implant 142 of FIG. 10 includes an elongate trunk 144 formed with one or more recesses 146 that extend inwardly through a portion of the outer surface 308. The recesses 146 are sized to receive the injectable material(s). The recesses 146 are positioned between the proximal end 302 and the distal end 304 of the trunk 144. The implant 142 may be positioned within the patient such that the recess 146 is positioned near or adjacent the interface 326 between the first and second tissue sections 122, 124.

Figure 11:
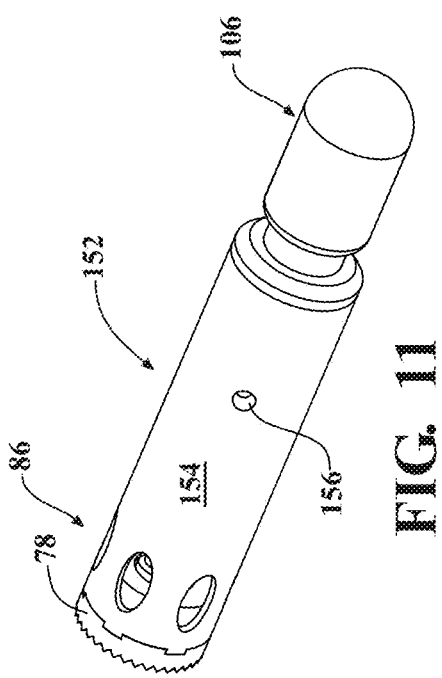
FIG. 11 is a perspective view of an implant in accordance with another exemplary embodiment of the present disclosure.

FIG. 11 shows an implant 152 in accordance with another exemplary embodiment of the present disclosure. In at least many respects the implant 152 of the present embodiment is the same as that previously described. The implant 152 of FIG. 11 includes the trunk 154 formed with one or more orifices 156 (one shown). The orifices 156 extend inwardly from the outer surface of the trunk 154 and in fluid communication with bore 102. The implant 152 may be positioned within the patient such that the orifices 156 are positioned near or adjacent the interface 326 between the first and second tissue sections 122, 124. In one example, when injectable material is injected into the bore 102, at least a fraction of the injectable material flows out of the orifices 156. In another example to be described (see FIG. 13B), a cannula 190 may be selectively positioned to cause the injectable material to be directed through the orifices 156. It is contemplated that the orifices 156 of FIG. 11 may be provided in addition to the recesses 146 of FIG. 10.

Figure 12:
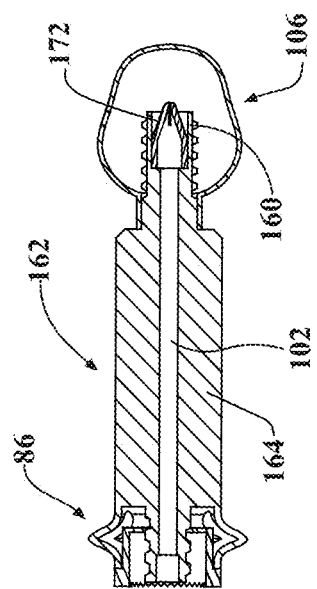
FIG. 12 is a cross section view of an implant in accordance with another exemplary embodiment of the present disclosure.

Referring now to FIG. 12, another exemplary implant 162 includes the trunk 164 defining the bore 102. A valve 172 may be in communication with the distal end of the bore 102, for example, coupled within the head 168 of the implant 162. In the illustrated embodiment, the valve 172 is a duck-billed valve. To facilitate the fitting of valve 172, internal to the head 94 of the trunk 164 there is a counterbore 160 with the bore 102 opening into the counterbore 160. The counterbore 160 is shaped to receive the valve 172. The valve 172 is configured to allow fluid flow from bore 102 into the interior 314 within expandable member 312 while blocking fluid flow in the reverse direction.

Figure 13A:
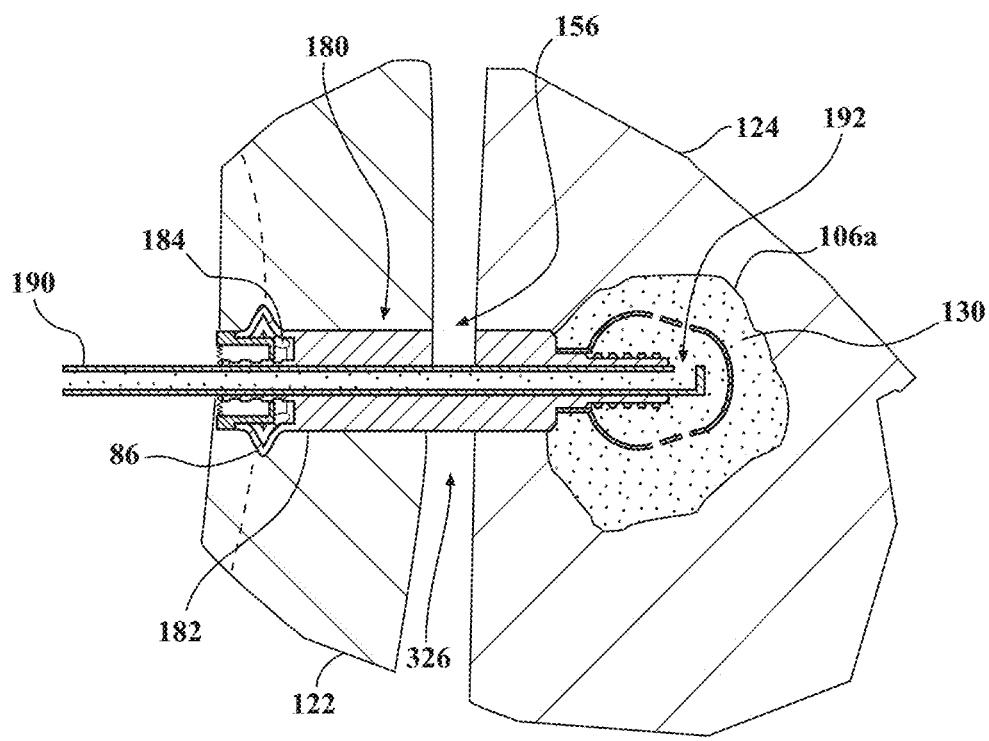
FIGS. 13A, 13B and 13C is a cross sectional view of the implant within the first and second tissue sections, as shown in FIG. 9, and further illustrating directing of material(s) into or between the first and second tissue sections at various points along a length of the implant.
Figure 13B:
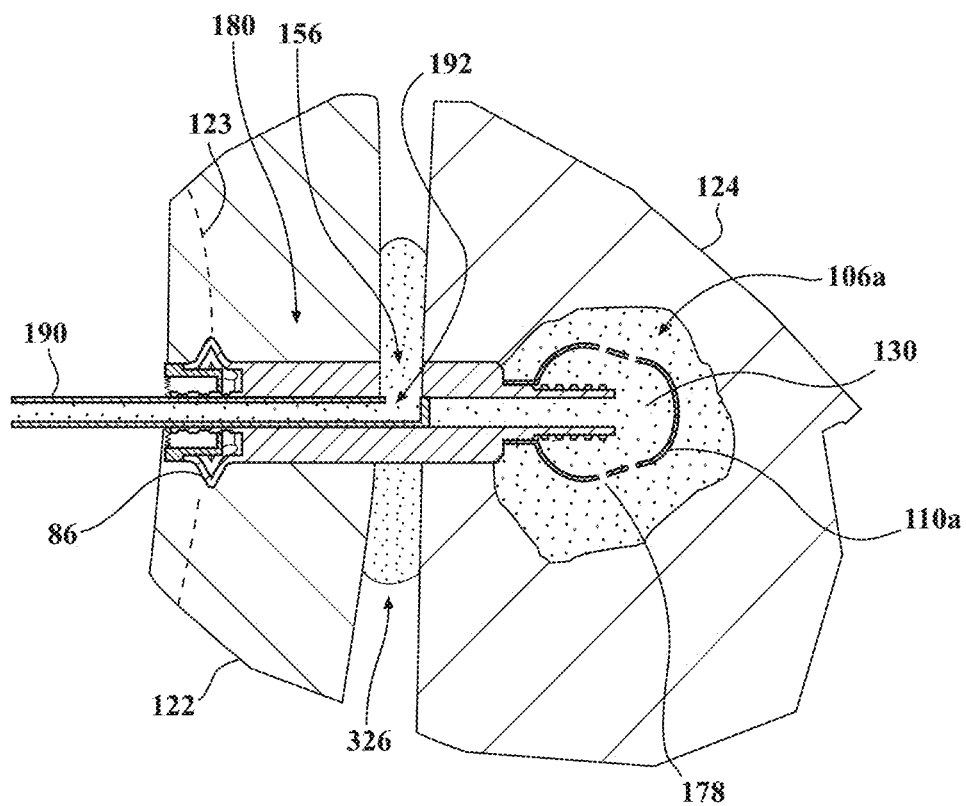
Figure 13C:
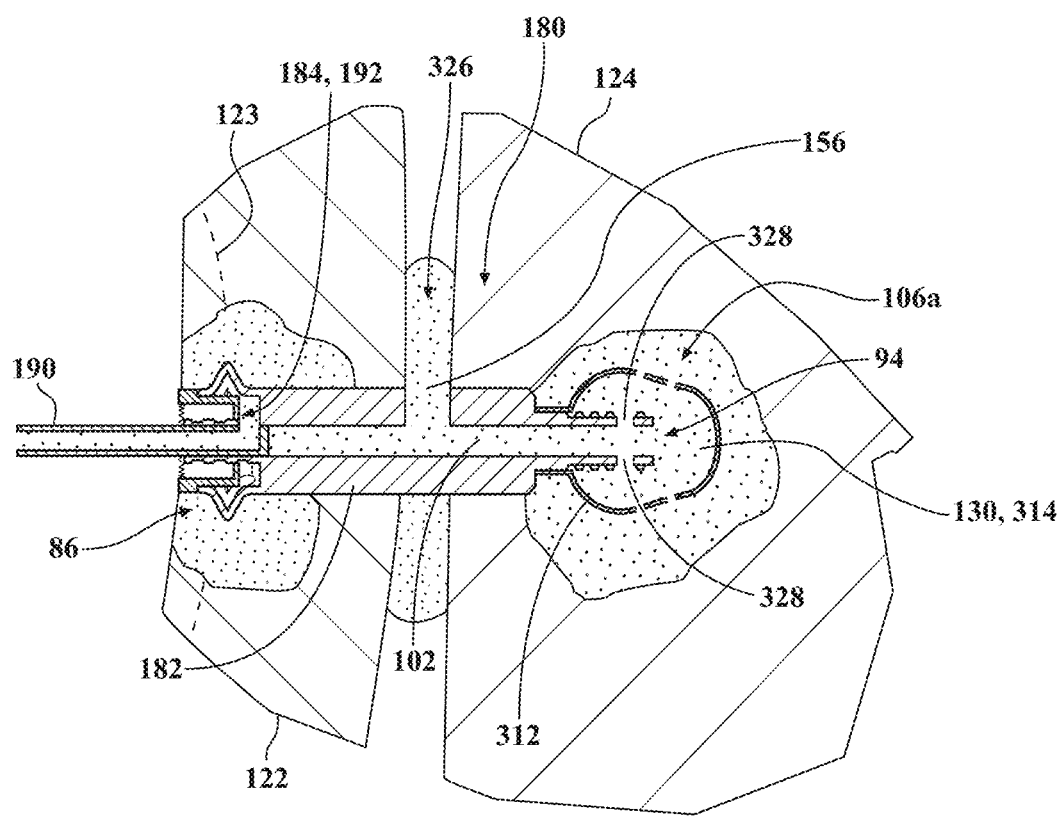

In certain embodiments, the injectable material may be introduced at different locations along the length of the implant 76. This would allow the injectable material to selectively be introduced into the distal anchor 106, through the orifices 156 in the trunk 90, and/or through the apertures 104 of the proximal anchor 86. FIGS. 13A, 13B and 13C illustrate an implant 180 with which this type of cannula may be used. For clarity, the figures show the first and second tissue sections 124, 124 spaced apart from one another. In at least many respects the implant 180 of the present embodiment is the same as that previously described. The implant 180 of the present embodiment includes an elongate trunk 182 with the orifice(s) 156 previously described. The implant 180 may further include additional pathways 184 defined between the apertures 104 of the proximal anchor 86 prior to or after buckling of the deformable features 310.

A cannula 190 is slidably disposed in the bore 102 formed in trunk 182. It is to be understood that the delivery cannula 68 of FIG. 4 may alternatively be used. The cannula 190 includes a proximal inlet port configured to be in fluid communication with a source of injectable material, and an outlet port 192. The cannula 190 may be formed so the distal end of the cannula 190 is closed, and the outlet port 192 is a side port. For example, FIGS. 13A to 13C show the closed distal end and the outlet port immediately proximal to the closed distal end.

The implant 180 may be suitably positioned within the first and second tissue sections 122, 124. As seen in FIG. 13A, the cannula 190 is directed through the bore 102 to position the outlet port 192 distal to the head 94 and within the interior 314 of the expandable member 312a. The curable material is flowed through the cannula 190 and outlet port 192 into the expandable member 312a. The injectable material first expands the expanding portion 110a of the expandable member 312a. Since expandable member 312a is formed with pores 178 (and/or fenestrations), the continued flow of curable material into the expandable member 312a causes the curable material to flow out of the pores 178 and into the borehole 126 and the surrounding surface of the second tissue section 124. Subsequent to the curable material curing external to the expandable member 312a, within the interior 314, and through the pores 178 (and/or fenestrations), the interaction (e.g., retention) of the distal anchor 106 and the second tissue section 124 is improved.

Referring now to FIG. 13B, the cannula 190 is axially positioned so the outlet port 192 is in fluid communication with the orifice 156. Material(s) to be introduced into the interface 326 or joint space between the sections of first and second tissue sections 122, 124. For example, the injectable material may be the curable material, the bone growth material, and/or the therapeutic agent. It is understood that the interface 326 or joint space is comprised of cartilaginous material with synovial space not particularly conductive to receiving injected material. In certain exemplary methods, anatomy from the interface 326 or joint space may be removed prior to injecting the material(s). For example, the joint space may be decorticated (i.e., removing outer layers of cartilage to expose the surfaces of the first and second tissue sections 122, 124). The decortication may be performed with a mechanical instrument such as a curette. The instrument may be directed through a portion of the borehole 126 and into the interface 326 prior to positioning the implant 76 within the borehole 126 (e.g., during or subsequent to creation of the borehole 126). In another example, a working end of instrument may be sized to be extend through the orifice(s) 156 of the implant 76. With the implant 76 suitably positioned within the borehole 126, the working end of the instrument is directed through the orifice(s) 156 to decorticate the interface 326. The implant 76 may be rotated within the borehole 126 (with the proximal and distal anchors 86, 106 in the initial configuration and collapsed state, respectively) with the working end of the instrument extend through the orifice(s) 156 to decorticate the interface 326. With the surfaces of the first and second tissue sections 122, 124 exposed, the injected material(s), for example the bone growth material, directly contacts the bone surfaces to promote bone growth and fusion.

The cannula 190 may be positioned so that outlet port 192 is placed in fluid communication with the orifice 184, as shown in FIG. 13C. The injectable material may be introduced to the additional pathways 184 defined between the apertures 104 of the proximal anchor 86 prior to or after buckling of the deformable features 310. In one example, the additional curable material introduced through the pathways 184, upon hardening, strengthens the fixation of the proximal anchor 86 to the first tissue section 122. Further, it is contemplated that the cannula 190 may be replaced with another cannula to inject different types of materials to different locations along the length of the implant 180.

Figure 14:
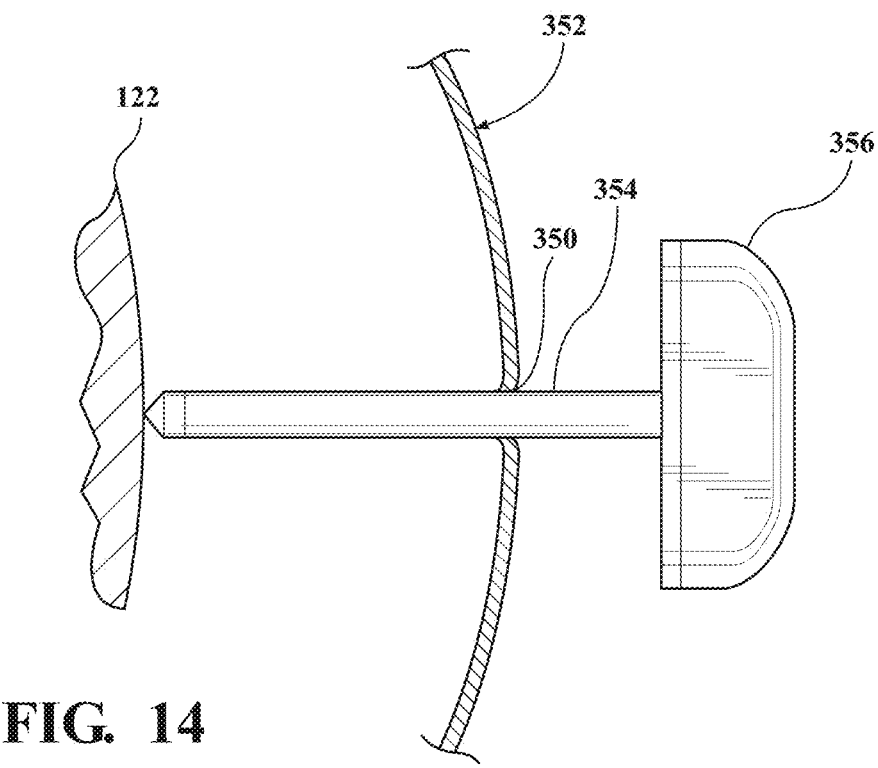
FIG. 14 is an elevation view of an access cannula and access needle positioned through an incision within skin.

FIGS. 14-18 show several steps of an exemplary method for preventing relative motion between the first and second tissue sections 122, 124. The first tissue section 122 is hereinafter referred to as the ilium 122, and the second tissue section 124 is hereinafter referred to as the sacrum 124 of the patient. The implant 76 is implanted using a minimally invasive procedure. First, a minimally invasive incision 350 (see FIG. 18) is created in the skin 352 of the patient. The incision 350 may be formed with a scalpel, the access needle 356 disposed inside the access cannula 354, or by other methods. The access cannula 354 with the access needle 356 is directed through the overlying soft tissue towards the ilium 122. The overlying soft tissue is dilated, and a distal end of the access cannula 354 is positioned near or adjacent the ilium 122 as shown in FIG. 14. The access needle 356 may be removed to provide a working channel through the access cannula 354 to the ilium 122.

As previously described, the guidewire (not shown) may be provided to facilitate creation of the borehole 126. The guidewire is directed through the working channel and into engagement with the ilium 122. The access cannula 354 may be removed with the guidewire remaining in engagement with the ilium 122 and extending above the skin 352 of the patient. The drill 358, the tool 30, and the implant 76 being cannulated to receive the guidewire with the subsequent steps performed with the access cannula 354 removed.

Figure 15:
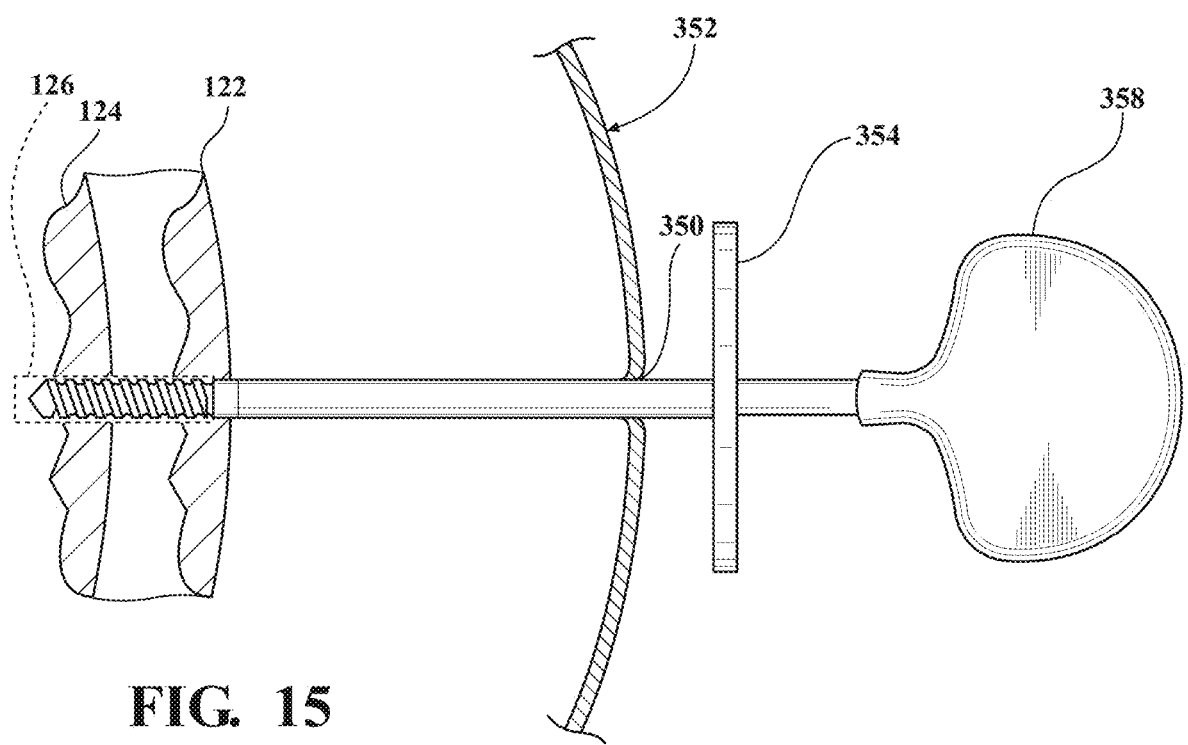
FIG. 15 is an elevation view of an access cannula of FIG. 14 with a drill used to resect a borehole in the first and second tissue sections.

Referring to FIG. 15, the drill 358 is inserted through the access cannula 354 to engage the ilium 122. The drill 358 is operated to resect the borehole 126 through the ilium 122 and into the sacrum 124, after which the drill 358 is removed from the access cannula 354. FIG. 15 shows the drill with a handle configured to be hand-operated, but it is understood that powered drills, burs, shavers, and the like, may be used to resect the borehole 126.

Figure 16:
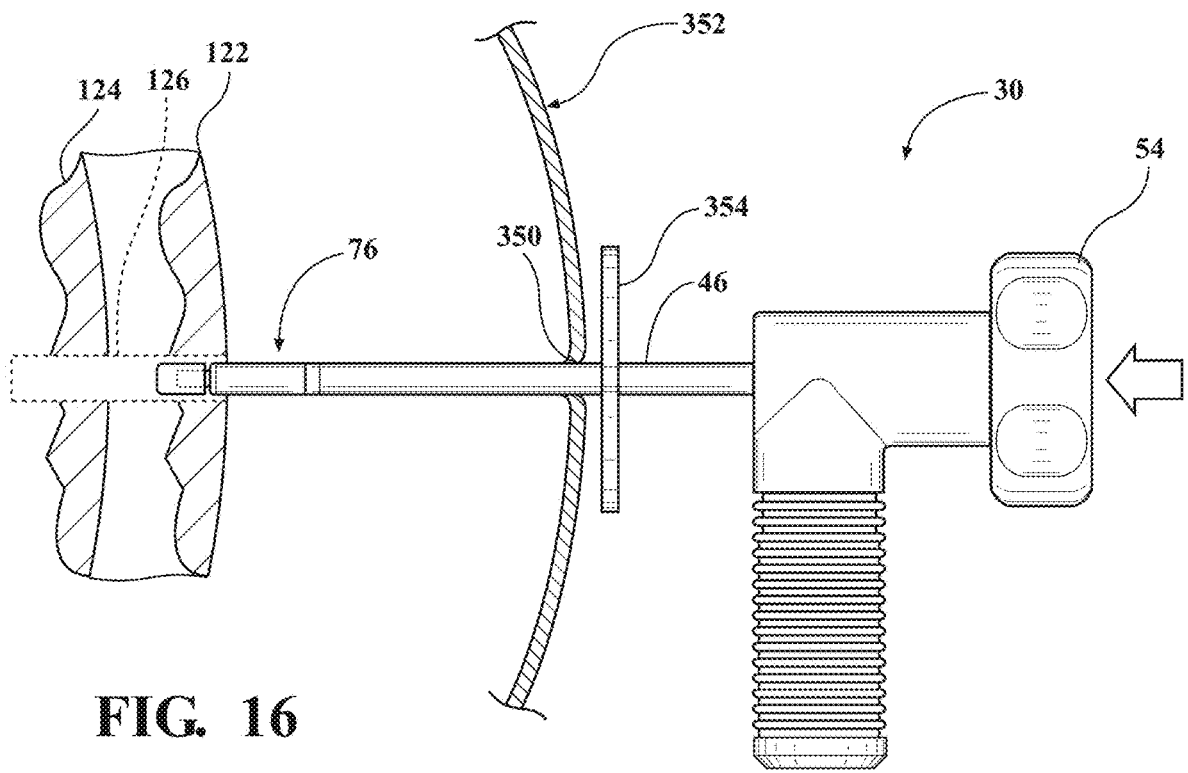
FIGS. 16 and 17 illustrate steps of positioning the implant through the access cannula and into the borehole using the insertion tool.

FIG. 16 shows the tool 30 is provided with the implant 76 removably coupled to the distal end of the shaft 46. In some embodiments, a single tool 30 is used throughout the procedure and the method may include a step of removably coupling the implant 76 to the tool 30. In this embodiment, the tool 30 is operated by applying a torque to the driver 52 in a first direction to engage drive features (e.g., the threads 64), of the drive shaft 60 of the tool 30 with complimentary driven features (e.g., the threads 89) coupled to the stem 88. The tool 30 is further operated to engage engagement features, such as teeth 47, coupled to the shaft 46 of the tool 30 with complimentary engagement features (e.g., the teeth 81) coupled to the trunk 90 to prevent rotation of the proximal anchor 86 relative to the shaft 46 and prevent an axial movement of the proximal end of the proximal anchor 86 relative to the shaft 46. Further, the delivery cannula 68, which is coaxially disposed within the lumen 62 is placed in fluid communication with the bore 102.

Figure 17:
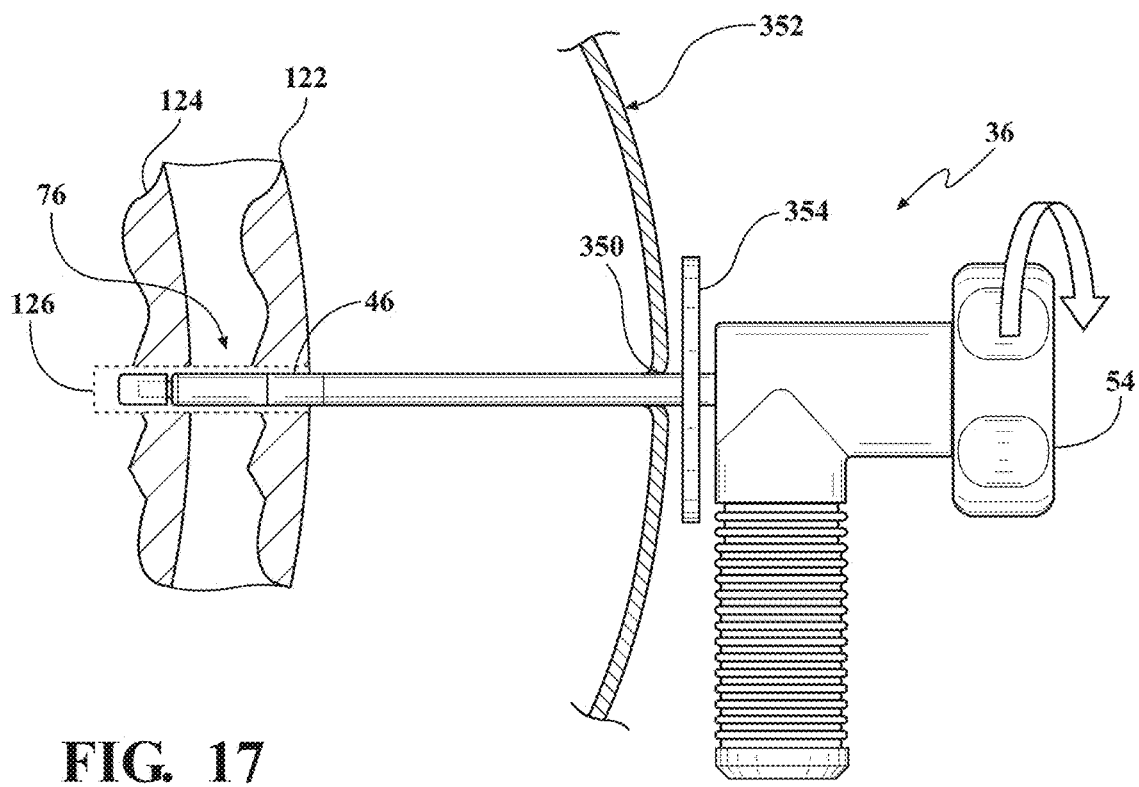

FIGS. 16 and 17 illustrate the steps of positioning the implant 76 within the borehole 126 such that the proximal anchor 86 is disposed in the ilium 122 and the distal anchor 106 is disposed in the sacrum 124, and operating an insertion tool 30 to apply a compressive force to the proximal anchor 86 along the longitudinal axis 300 to move the proximal anchor 86 from the initial configuration to the deployed configuration. The implant 76 may be positioned within the borehole 126 such that the expandable member 312 is disposed within the cancellous bone of the sacrum 124. Prior to applying the compressive force to the proximal anchor 86, the deformable feature 310 is within the periphery 306 of the trunk 90. The compressive force is applied by rotating the knob 54 in a first direction (represented by the arrow shown in FIG. 17). The rotation of the knob 54 in turn rotates the drive shaft 60, which due to the engagement of the threads 64 on the drive shaft 60 and the threads 89 on the stem 88, the stem 88 is drawn into the lumen 62. Because rotation of the proximal anchor 86 relative to the shaft 46 and axial movement of the proximal end of the proximal anchor 86 relative to the shaft 46 is prevented, the compressive force is applied to the deformable feature 310. The compressive force deforms the deformable feature 310 such that at least a portion of the deformable feature 310 extends outwardly beyond the periphery 306 of the trunk 90 relative to the longitudinal axis 300 to engage the ilium 122.

Once the proximal anchor 86 is engaged and maintaining the position of the implant 76 relative to the ilium 122, the tool 30 may be decoupled from the implant 76. A torque is applied to the driver 52 of the tool 30 in a second direction opposite to the first direction (represented by the arcuate arrow shown in FIG. 18) to rotate the drive shaft 60. The proximal anchor 86 is in the deployed configuration and engaging the ilium 122, and rotation of the drive shaft 60 decouples the threads 64 from the complimentary threads 89 of the implant 76. When the distal end of the shaft 46 of the tool 30 is decoupled from the implant 76, the delivery cannula 190 (or the delivery cannula 68) remains coupled to the implant 76 positioned within the borehole 126, as shown in FIG. 18. The presence of the delivery cannula 190 extending above the incision 350 in the skin 352 provides visual indication to the surgeon of the presence, location, and orientation of the implant 72 within the patient.

After the proximal anchor 86 is engaged and maintaining the position of the implant 76 relative to the ilium 122, the distal anchor 106 is engaged with the sacrum 124. The injectable material is injected from the source of injectable material. In order to inject the injectable material, an injectable material delivery system 360 includes or is coupled to the source of injectable material. One such injectable material delivery system 360 is shown in FIG. 18. The injectable material delivery system 360 is coupled to the cannula 190 such that injectable material injected into the cannula 190 flows through the bore 102 and into the interior 314 of the expandable member 312. The injectable material moves the expandable member 312 between the collapsed state in which the expandable member 312 is within the periphery 306 of the trunk 90, and the expanded state in which at least a portion of the expandable member 312 extends outwardly beyond the periphery 306 of the trunk 90 relative to the longitudinal axis 300. Owing to the porosity of the cancellous bone, the expandable member 312 (and in certain embodiments the injectable material directed through porous features or fenestrations 178 of the expandable member 312), displace blood and marrow forming the cancellous bone. In embodiments where the injectable material is curable material, the curable material is permitted to cure within the interior 314 of the expandable member 312 with the expandable member 312 engaging the sacrum 124. Additionally, the curable material injected into the interior 314 of the expandable member 312 surrounds the neck 92 and is in contact with the rib 96. The curable material is permitted to cure in contact with the rib 96 to facilitate axial retention of the implant 76 within the cured curable material.

In some embodiments of the method, the expandable member 312 comprises fenestrations 178. In this embodiment the method further comprises a step of injecting additional curable material into the interior 314 of the expandable member 312 such that a portion of the curable material is urged through the fenestrations 178 and into contact with the sacrum 124. In another embodiment of the method, the expandable member 312 is formed from a permeable material. In this embodiment the method further comprises a step of injecting additional curable material into the interior 314 of the expandable member 312 such that a portion of the curable material is urged through the permeable material and into contact with the sacrum 124.

In some embodiments of the method, multiple implants 76 may be implanted into a patient. As mentioned above, each implant 76 may have as dedicated tool 30, or a single tool 30 may be used to insert multiple implants 76. The method further comprises the step of decoupling the tool 30 from a first implant, and removably coupling the tool 30 to a second implant. With continued reference to FIG. 18, the second implant is then inserted through a second minimally invasive incision and within a second borehole with a proximal anchor of the second implant engaging the ilium 122 and a distal anchor of the second implant disposed in the sacrum 124. The proximal anchor of the second implant is then deployed in a manner substantially the same as the first implant. Prior to both the first implant and second implant receiving the injectable material, the second implant is decoupled from the distal end of the shaft 46 of the installation tool 30 with a second delivery cannula remaining coupled to the second implant positioned within the second borehole. The delivery cannulas coupled to the first and second implants extend through the first and second minimally invasive incisions, respectively. The injectable material is then injected into each delivery cannula to expand the expandable member of the first implant and the second implant.

After expanding the expandable member 312 of the one or more implants 76 outwardly to engage the sacrum 124, the delivery cannula 68 and the access cannula 354 are each removed through the minimally invasive incision 350. Finally, the minimally invasive incision 350 is closed with the expandable member 312 and cured curable material remaining within the patient.

The foregoing is directed to specific versions of the disclosure. Other features of the stabilization system and/or the implant are contemplated. For example, the shapes of the components of the implant 76 may vary from what has been described. In alternative versions of the disclosure the trunk 90 may be non-circular in cross section. In some of these versions of the disclosure the trunk 90 may be formed so as to have straight edges that meet at corners. A benefit of providing the trunk 90 with non-circular cross-sectional shapes is that it can serve to limit the rotation of the implant 76 in the tissue in which the implant 76 is seated. In certain embodiments, certain structures of the implant 76 may be formed of unitary construction (e.g., the trunk 90 and the cap 78). Likewise, for ease of manufacture, it may be desirable to form the trunk 90 out of coaxial inner and outer tubes. Further, in certain embodiments, the trunk 90 may be curved or angled along a curved longitudinal axis 300. This feature may be useful to facilitate placement of the implant 76 or the mechanical properties of the implant 76. In certain embodiments, one or both of the proximal and distal anchors 86, 106, may be configured to deploy asymmetrically. This would be particularly suitable for applications where space considerations are present in the intended area of the implant. Additionally or alternatively, the implant 76 may be configured to withstand asymmetric mechanical loading. In certain embodiments, the proximal and distal anchors 86, 106 of the implant 76 of may be configured to be deployed either simultaneously or sequentially.

In certain embodiments, the proximal anchor 86 may not extend beyond the periphery 306 in the deployed configuration, and/or the distal anchor 106 may not extend beyond the periphery 306 in the expanded state. The deployed configuration and the expanded state may be alternatively defined as the proximal anchor 86 and the distal anchor 106, respectively, simply moving radially outwardly from the longitudinal axis 300 of the trunk 90 (even if not beyond the periphery 306).

The proximal anchor 86 may be of any suitable construction. For example, a screw-like member may be provided with a threaded shaft having a pointed tip. The screw-type member is deployed by rotating the anchor so the shaft threads into the bone. The shaft threading engages the bone to secure the anchor and, by extension, the implant to the bone. For another example, one or more rigid pins may be provided to deploy by being forced outwardly from the trunk. Another alternative includes a spring that is under tension with the anchor deployed by releasing a member restraining the spring.

Likewise, the distal anchor 106 may be of any suitable construction. In certain embodiments, the expandable member 312 is formed from a non-compliant material that inflates to a defined shape. An example of a non-compliant material is a synthetic textile such as woven polyester fabric. An outer surface of the expandable member 312 may be impregnated with materials. One such material may be a material to encourage bone growth, and another material may include the therapeutic agent (e.g., a material that reduces the likelihood of infection). It should be understood that that the distal anchor may take the form of an outwardly buckling assembly and the proximal anchor take the form of an inflatable expandable member.

The tool 30 may include the additional and/or alternative components for deploying the implant 76. These components may include solid shafts that are moved longitudinally relative to the tool handle 32. Each shaft is advanced or retracted to deploy the anchor that the shaft engages. Likewise, other means than threading may be used to releasably hold the implant 76 to the tool 30. For example, for some versions of the disclosure, the tool 30 may be formed with fingers that retract or contract. The implant 76 is formed with complementary openings for receiving the distally located tips of these fingers. Once the implant 76 is set the fingers are retracted or contracted away from the openings in which they are seated so as to disconnect the tool 30 from the implant 76.

The cannula (e.g., the delivery cannula 86 or the cannula 190) itself may be comprised of a flexible material to allow the cannula to exit the opening and deliver injectable material distally of the implant 76 through that opening. For example, cannula may be comprised of a superelastic metallic material, such as nitinol, that possesses a preset curved shape that allows it to exit the opening in the implant 76 and deliver injectable material to a tissue location a certain distance away from the implant 76. It is further contemplated that another instrument may be deployed through the bore 102, for example, a curette that is used to form a cavity around the implant 76.

Variations in the above described exemplary methods are also contemplated. The borehole 126 in which the implant is fitted may have a diameter equal to or less than the diameter of the trunk 90 of the implant 76. For example, the diameter of the borehole 126 is less than the diameter of the trunk 90, by 1 mm or less. In such an example, there is a compression or interference fit between the trunk 90 and the tissue surrounding the trunk 90. In certain methods, the tool 30 are arranged to hold the trunk 90 of the implant 76 static while the tool 30 is advanced distally (as opposed to retracted proximally) to provide the compressive force to induce buckling of the proximal anchor 86. Further, it is also contemplated that the adjacent sections of soft tissue may be secured together. For example, the implant 76 may include one or more barbs.

The foregoing is directed to specific versions of the disclosure. Other versions of the disclosure may have different features. It should likewise be understood that not all versions of the disclosure may have each of the above described features. Likewise, the features of the different versions of the disclosure may be combined. Accordingly, it is an object of the appended claims to cover all such variations and modifications that come within the scope of this disclosure.

The invention claimed is:

1. A system for preventing relative motion between bones or sections of bone, the system comprising:
   an insertion tool comprising a handle, a driver coupled to the handle, a tool shaft extending from the handle and comprising a first engagement feature, and a drive shaft disposed within the tool shaft and operably coupled to the driver, wherein the drive shaft comprises a drive feature; and
   an implant removably coupled to the insertion tool and comprising a trunk, a distal anchor, a proximal anchor, a skirt defining a cavity and comprising a second engagement feature configured to be engaged by the first engagement feature of the tool shaft to prevent relative rotation between the implant and the insertion tool, and a stem disposed within the cavity and coupled to a proximal end of the trunk that is at an axial position distal to the proximal anchor, wherein the stem comprises a driven feature configured to be engaged by the drive feature of the drive shaft,
   wherein the driver is configured to receive an input for the drive shaft to draw the stem proximally such that the trunk is drawn towards the insertion tool, and wherein the drawing of the trunk and engagement of the first and second engagement features is configured to deploy the proximal anchor outwardly.

2. The system of claim 1, wherein the driver is a knob, wherein the drive feature and the driven feature are complementary threading, and wherein rotation of the knob is configured to rotate the drive shaft to draw the stem proximally.

3. The system of claim 1, wherein the proximal anchor further comprises deformable features interposed between adjacent pairs of apertures, and wherein the drawing of the trunk against resistance from the insertion tool is configured to induce deformation of the deformable features by compressive loading.

4. The system of claim 1, wherein the first engagement feature is teeth annularly disposed about a distal end of the tool shaft.

5. The system of claim 1, wherein a distal end of the drive shaft is located distally forward to the distal end of the tool shaft.

6. The system of claim 1, wherein the trunk defines a bore, and wherein the drive shaft defines a lumen configured to be arranged in fluid communication with the bore with the implant removably coupled with the insertion tool.

7. The system of claim 6, wherein the lumen of the drive shaft is sized to be seated over the stem.

8. The system of claim 6, wherein the distal anchor is an expandable member, wherein the system further comprises a delivery cannula configured to be slidably disposed within the lumen of the drive shaft and further configured to inject injectable material into the expandable member to deploy the distal anchor.

9. The system of claim 6, wherein the trunk defines at least one orifice in fluid communication with the bore, wherein injectable material directed through the bore is configured to be further directed through the at least one orifice and into adjacent tissue.

10. The system of claim 1, wherein an outer surface of the trunk defines at least one recess configured to receive injectable material.

11. The system of claim 1, wherein the insertion tool and the implant are cannulated, the system further comprising:
a guidewire; and
a cannulated drill configured to be directed over the guidewire to form a borehole within which the implant is configured to be implanted,
wherein the insertion tool and the implant are further configured to be directed over the guidewire to position the implant within the borehole.

12. A system for preventing relative motion between bones or sections of bone, the system comprising:
an insertion tool comprising a handle, a driver coupled to the handle, a tool shaft extending from the handle, and a drive shaft disposed within the tool shaft and operably coupled to the driver, wherein the drive shaft defines a lumen; and
an implant removably coupled to the insertion tool and comprising a trunk, a distal anchor comprising an expandable member, and a proximal anchor configured to be deployed by the drive shaft based on an input to the driver,
wherein the implant defines a bore extending through the proximal anchor and configured to be arranged in fluid communication with the lumen of the drive shaft for injectable material to be directed from the lumen and through the bore to within the expandable member to deploy the distal anchor,
wherein the implant further comprises a stem coupled to a proximal end of the trunk, and wherein the bore extends through the stem.

13. The system of claim 12, wherein a proximal end of the stem defines a counterbore in fluid communication with the bore, wherein the system further comprises a delivery cannula sized to be directed through the lumen to be seated within the counterbore.

14. The system of claim 12, wherein the trunk defines at least one orifice in fluid communication with the bore, wherein the injectable material directed through the bore is configured to be further directed through the at least one orifice and into adjacent tissue.

15. A system for preventing relative motion between bones or sections of bone, the system comprising:
a guidewire;
an insertion tool comprising a handle, a driver coupled to the handle, a tool shaft extending from the handle, and a drive shaft disposed within the tool shaft and operably coupled to the driver, wherein the insertion tool is cannulated; and
an implant removably coupled to the insertion tool and comprising a trunk, a distal anchor, a proximal anchor, wherein the implant defines a bore extending through the proximal anchor and the trunk, and wherein the distal anchor defines an inner passageway coaxially arranged with the bore such that the implant is cannulated and configured to be directed with the insertion tool over the guidewire to position the implant within a borehole,
wherein the proximal anchor configured to be deployed by the drive shaft based on an input to the driver, and wherein the distal anchor is configured to be deployed independently from deployment of the proximal anchor.

16. The system of claim 15, further comprising a cannulated drill configured to be directed over the guidewire to form the borehole.

17. The system of claim 15, wherein the distal anchor is a toroidal expandable member.

18. The system of claim 17, wherein the implant further comprises a neck extending from the trunk and to which the toroidal expandable member is coupled, and wherein the neck extends through an entirety of a length of the toroidal expandable member.

* * * * *